United States Patent
Klosin et al.

(10) Patent No.: US 10,301,412 B2
(45) Date of Patent: May 28, 2019

(54) FIVE-COORDINATE BIS-PHENYLPHENOXY CATALYSTS FOR THE PREPARATION OF ETHYLENE-BASED POLYMERS

(71) Applicant: Dow Global Technologies LLC, Midland, MI (US)

(72) Inventors: Jerzy Klosin, Midland, MI (US); Endre Szuromi, Richwood, TX (US); Liam P. Spencer, Manvel, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/518,672

(22) PCT Filed: Dec. 2, 2015

(86) PCT No.: PCT/US2015/063312
§ 371 (c)(1),
(2) Date: Apr. 12, 2017

(87) PCT Pub. No.: WO2016/089935
PCT Pub. Date: Jun. 9, 2016

(65) Prior Publication Data
US 2017/0267796 A1 Sep. 21, 2017

Related U.S. Application Data

(60) Provisional application No. 62/087,621, filed on Dec. 4, 2014.

(51) Int. Cl.
| C08F 4/64 | (2006.01) |
| C08F 4/76 | (2006.01) |
| C08F 210/16 | (2006.01) |
| C07F 7/00 | (2006.01) |
| B01J 31/22 | (2006.01) |
| C08F 4/659 | (2006.01) |

(52) U.S. Cl.
CPC ............ *C08F 210/16* (2013.01); *C07F 7/00* (2013.01); *B01J 31/223* (2013.01); *B01J 2531/46* (2013.01); *B01J 2531/48* (2013.01); *B01J 2531/49* (2013.01); *B01J 2540/40* (2013.01); *C08F 4/659* (2013.01); *C08F 4/65908* (2013.01); *C08F 4/65912* (2013.01)

(58) Field of Classification Search
CPC ............ C08F 4/60189; C08F 4/64189; C08F 4/60193; C08F 4/64193; C08F 210/16
See application file for complete search history.

(56) References Cited

U.S. PATENT DOCUMENTS

| 8,058,373 B2 | 11/2011 | Stevens et al. |
| 8,202,953 B2 | 6/2012 | Konze et al. |
| 8,299,189 B2 | 10/2012 | Boone et al. |
| 8,354,484 B2 | 1/2013 | Konze et al. |
| 8,420,760 B2 | 4/2013 | Hughes et al. |
| 8,450,438 B2 | 5/2013 | Aboelella et al. |
| 8,772,414 B2 | 7/2014 | Liang et al. |
| 9,102,824 B2 | 8/2015 | Liang et al. |
| 9,175,107 B2 | 11/2015 | Diamond et al. |
| 9,534,070 B2 | 1/2017 | Spencer et al. |
| 2008/0051537 A1 | 2/2008 | Carnahan et al. |
| 2011/0282018 A1 | 11/2011 | Klosin et al. |
| 2012/0095158 A1 | 4/2012 | Patel et al. |
| 2012/0129417 A1 | 5/2012 | Taha et al. |
| 2013/0071663 A1 | 3/2013 | Ludtke et al. |
| 2013/0144018 A1* | 6/2013 | Klosin ................ C07D 209/82 526/136 |
| 2015/0322185 A1 | 11/2015 | Li Pi Shan |

FOREIGN PATENT DOCUMENTS

| WO | 2003091262 A1 | 11/2003 |
| WO | 2011/146044 A1 | 11/2011 |
| WO | 2013/096573 A1 | 6/2013 |
| WO | WO 2013/101375 A1 * | 7/2013 ............ C08F 10/00 |

OTHER PUBLICATIONS

Bringmann, Tetrahedron Asymmetry, 2003, vol. 14, No. 15, p. 2225-2228.
PCT/US2015/063312, International Search Report and Written Opinion dated Dec. 2, 2016.
PCT/US2015/063312, International Preliminary Report on Patentability dated Jun. 15, 2017.

* cited by examiner

*Primary Examiner* — Rip A Lee
(74) *Attorney, Agent, or Firm* — Dinsmore & Shohl LLP

(57) ABSTRACT

The invention provides a molecular transition metal complex selected from Formula 1, as described herein; an ethylene-based polymer; and a process to form the ethylene-based polymer, said process comprising polymerizing ethylene in the presence of at least one molecular transition metal complex selected from Formula 1, as described herein, and wherein either $Z_1$ or $Z_2$ is dative covalent (coordinate) to the metal (M).

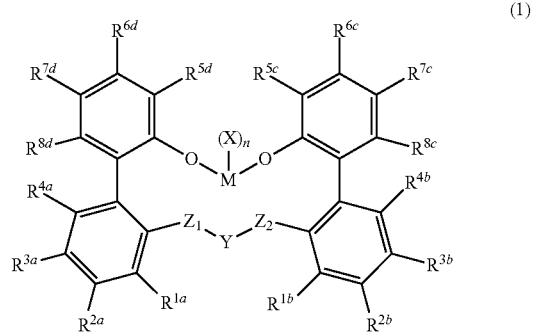

9 Claims, 1 Drawing Sheet

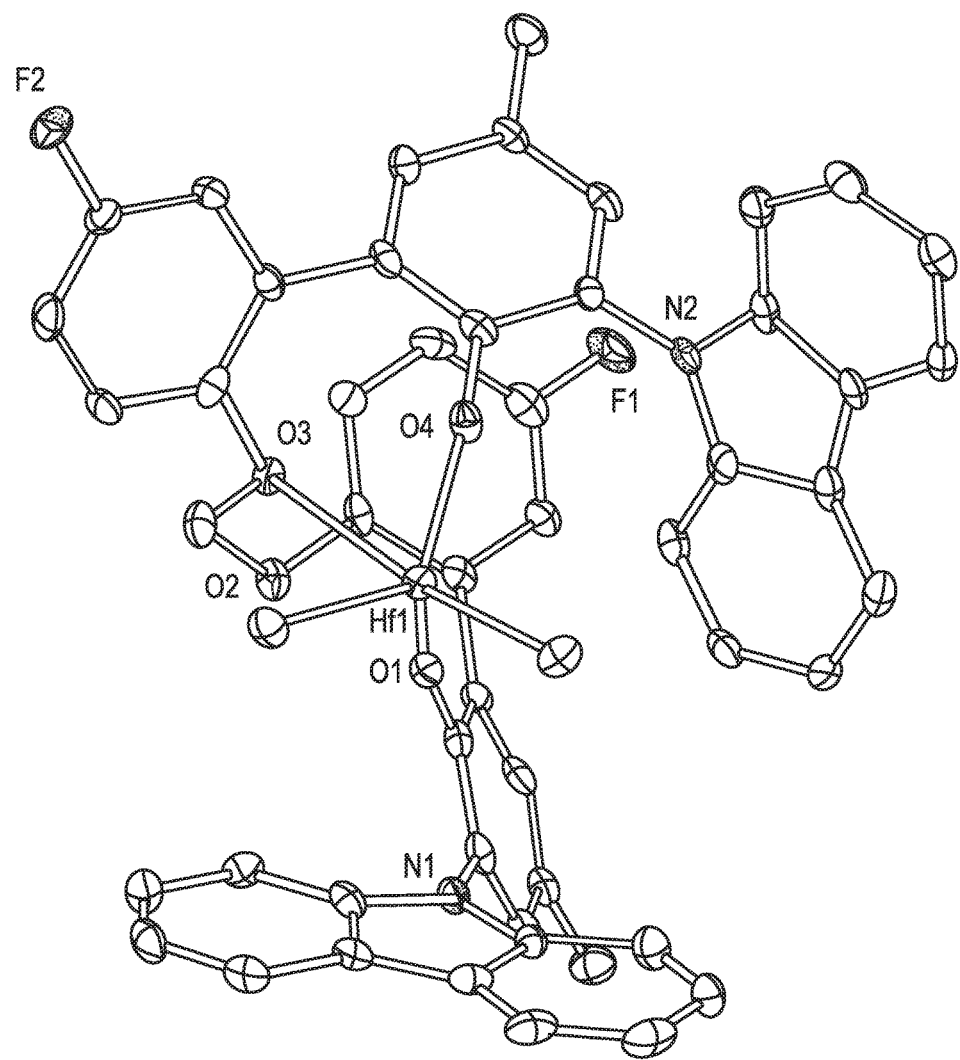

FIVE-COORDINATE BIS-PHENYLPHENOXY CATALYSTS FOR THE PREPARATION OF ETHYLENE-BASED POLYMERS

REFERENCE TO RELATED APPLICATIONS

The present application claims the benefit of U.S. Provisional Application No. 62/087,621, filed Dec. 4, 2014, and incorporated herein by reference.

BACKGROUND

Low molecular weight, semi-crystalline ethylene-based polymers (for example, weight average molecule weights less than 5,000 g/mole) can be used in formulations to make hot melt adhesives (for example, as wax components), and in other types of adhesives. Such polymers may be produced with conventional catalyst systems, for example, constrained geometry type catalyst systems or other bis-phenylphenoxy catalysts; however, typically significantly low polymerization temperatures are needed (<135° C.) to produce theses polymers. It is desirable to find new polymerizations using new catalyst systems, which are capable of making these low molecular weight, semi-crystalline polymers at elevated temperatures, with good efficiencies to allow for increased reactor throughput. This need has been met by the following invention.

SUMMARY OF THE INVENTION

The invention provides a molecular transition metal complex selected from Formula 1:

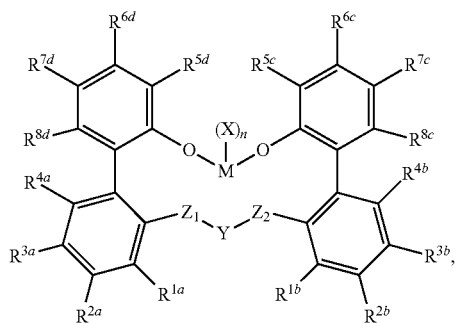

(Formula 1)

wherein M is titanium, zirconium, or hafnium, each independently being in a formal oxidation state of +2, +3, or +4;

n is an integer of from 0 to 3, wherein, when n is 0, X is absent;

each X is independently a monodentate ligand that is neutral, monoanionic, or dianionic, or two X are taken together to form a bidentate ligand that is neutral, monoanionic, or dianionic;

X and n are selected such that the metal-ligand complex is neutral;

$Z_1$ and $Z_2$ are each independently selected from the following: —O—, —S—, —N[($C_1$-$C_{40}$)hydrocarbyl]-, or —P[($C_1$-$C_{40}$)hydrocarbyl]-;

Y is a single atom bridge selected from the following: —$CR_2$—, —$GeR_2$—, —$SiR_2$—, —P—, —NR—; wherein each R is independently a hydrogen, a substituted or unsubstituted ($C_1$-$C_{40}$)hydrocarbyl, a substituted or unsubstituted ($C_1$-$C_{40}$)heterohydrocarbyl, —$OR^C$, —$SR^C$, —CN, —$CF_3$, —$OCF_3$, —S(O)$R^C$, —S(O)$_2R^C$, —N=C($R^C$)$_2$, —OC(O)$R^C$, —C(O)O$R^C$, —N(R)C(O)$R^C$, —C(O)N($R^C$)$_2$, or a halogen; and wherein each $R^C$ is independently a substituted or unsubstituted ($C_1$-$C_{30}$)hydrocarbyl, or a substituted or unsubstituted ($C_1$-$C_{30}$) heterohydrocarbyl; and wherein $R^{1a}$, $R^{2a}$, $R^{3a}$, $R^{4a}$, $R^{1b}$, $R^{2b}$, $R^{3b}$, $R^{4b}$, $R^{5c}$, $R^{6c}$, $R^{7c}$, $R^{8c}$, $R^{5d}$, $R^{6d}$, $R^{7d}$ and $R^{8d}$ are each, independently, selected from the following: a substituted or unsubstituted ($C_1$-$C_{40}$)-hydrocarbyl, a substituted or unsubstituted ($C_1$-$C_{40}$)heterohydrocarbyl, —Si($R^C$)$_3$, —OSi($R^C$)$_3$, —Ge($R^C$)$_3$, —P($R^C$)$_2$, —N($R^C$)$_2$, —$OR^C$, —$SR^C$, —$NO_2$, —CN, —$CF_3$, —$OCF_3$, —S(O)$R^C$, —S(O)$_2R^C$, —N=C($R^C$)$_2$, —OC(O)$R^C$, —C(O)O$R^C$, —N(R)C(O)$R^C$, —C(O)N($R^C$)$_2$, a halogen, or a hydrogen; and wherein each $R^C$ is independently a substituted or unsubstituted ($C_1$-$C_{30}$)hydrocarbyl, or a substituted or unsubstituted ($C_1$-$C_{30}$) heterohydrocarbyl; and wherein, for Formula 1, two or more of $R^{1a}$, $R^{2a}$, $R^{3a}$, $R^{4a}$, $R^{1b}$, $R^{2b}$, $R^{3b}$, $R^{4b}$, $R^{5c}$, $R^{6c}$, $R^{7c}$, $R^{8c}$, $R^{5d}$, $R^{6d}$, $R^{7d}$ and $R^{8d}$ may optionally form one or more ring structures; and wherein either $Z_1$ or $Z_2$ is dative covalent (coordinate) to M.

BRIEF DESCRIPTION OF THE DRAWINGS

FIG. 1 depicts the x-ray, molecular structure of CAT E (see experimental section). Hydrogens are omitted for clarity. The thermal ellipsoids are shown at the 50% probability level. (R1=2.6%).

DETAILED DESCRIPTION OF THE EMBODIMENTS

New molecular transition metal complexes have been discovered that contain a penta-coordinate metal (e.g., Hf, Zr or Ti) complex containing a single atom bridge structure, as described by the "Y" linkage of Formula 1 (discussed above) between two bridge structures described Z1 and Z2 of Formula 1 (discussed above). X-ray diffraction analysis revealed a penta-coordinate structure, in which one of the Z1 or Z2 atoms does not coordinate to the metal center, presumably due to strain imposed by such a short bridge. These complexes can be used to form low molecular weight ethylene-based polymers (for example, an Mw less than 5,000 g/mole), semi-crystalline (for example, Tm≥50° C.), with high catalyst activities and high reactor throughput.

As discussed above, the invention provides a molecular transition metal complex selected from Formula 1:

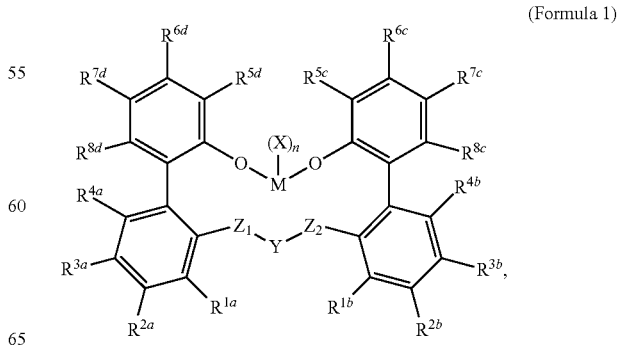

(Formula 1)

as described above.

The molecular transition metal complex of Formula 1 may comprise a combination of two or more embodiments as described herein.

In one embodiment, two or more of $R^{1a}$, $R^{2a}$, $R^{3a}$, $R^{4a}$, $R^{1b}$, $R^{2b}$, $R^{3b}$, $R^{4b}$, $R^{5c}$, $R^{6c}$, $R^{7c}$, $R^{8c}$, $R^{5d}$, $R^{6d}$, $R^{7d}$ and $R^{8d}$ do not form one or more ring structures.

In one embodiment, for Formula 1, $R^5$ and $R^{5d}$ are each, independently, selected from the following groups g1) through g14):

g1)
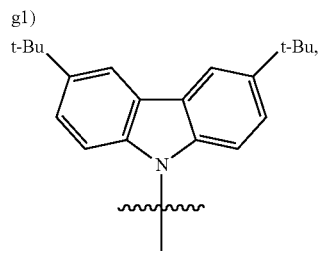

g2)
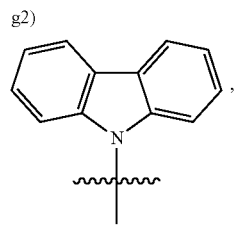

g3)
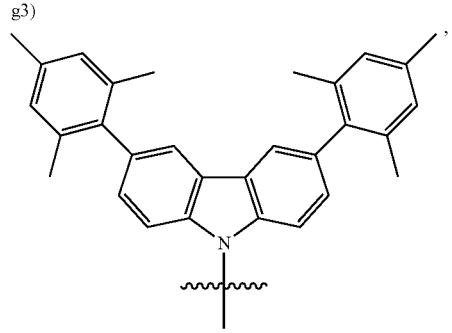

g4)
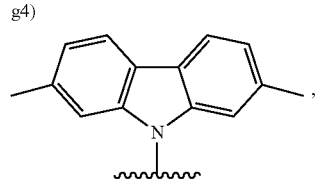

g5)
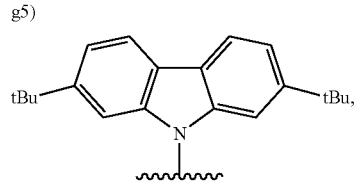

g6)
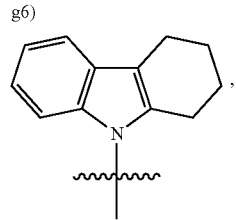

-continued (g7)
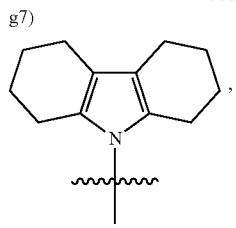

(g8)
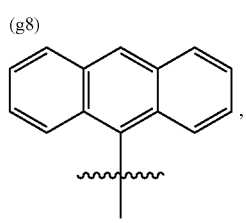

(g9)
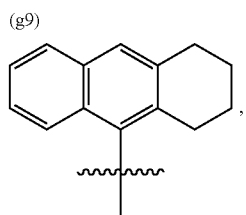

(g10)
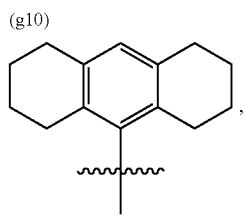

(g11)
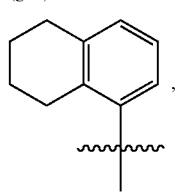

(g12)
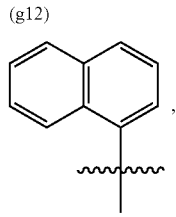

(g13)
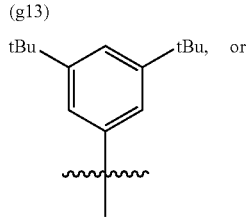

or

-continued (g14)

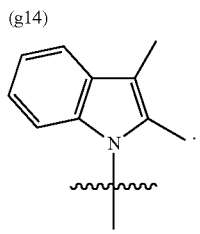

In structure g1) through g14), the external connection point of each substituent is indicated by a wavy line, as recommended by current IUPAC standards: *Pure Appl. Chem.*, 2008, 80, 277 (*Graphical representation standards for chemical structural diagrams*).

In one embodiment, for Formula 1, $R^{5c}$ and $R^{5d}$ are each, independently, selected from the following groups g1) through g4), g6), g8), g12), or g13).

In one embodiment, for Formula 1, $R^{5c}$ and $R^{5d}$ are each, independently, selected from the following groups g1), g2), g6), g5), or g13).

In one embodiment, for Formula 1, $R^{5c}$ and $R^{5d}$ are independently selected from the following: 1,2,3,4-tetrahydronaphthyl; anthracenyl; 1,2,3,4-tetrahydroanthracenyl; 1,2,3,4,5,6,7,8-octahydroanthracenyl; phenanthrenyl; 1,2,3,4,5,6,7,8-octahydrophenanthrenyl; 2,6-dimethylphenyl; 2,6-diisopropylphenyl; 3,5-di(tertiary-butyl)phenyl; 3,5-diphenylphenyl; 1-naphthyl; 2-methyl-1-naphthyl; 2-naphthyl; 1,2,3,4-tetra-hydronaphth-5-yl; 1,2,3,4-tetrahydronaphth-6-yl; anthracen-9-yl; 1,2,3,4-tetrahydroanthracen-9-yl; 1,2,3,4,5,6,7,8-octahydroanthracen-9-yl; 1,2,3,4,5,6,7,8-octahydrophenanthren-9-yl; indolyl; indolinyl; quinolinyl; 1,2,3,4-tetrahydroquinolinyl; isoquinolinyl; 1,2,3,4-tetrahydroisoquinolinyl; carbazolyl; 1,2,3,4-tetrahydrocarbazolyl; 1,2,3,4,5,6,7,8-octahydrocarbazolyl; 3,6-di(tertiary-butyl)-carbazol-9-yl; 3,6-di(tertiary-octyl)-carbazol-9-yl; 3,6-diphenylcarbazol-9-yl; 3,6-bis(2,4,6-trimethylphenyl)-carbazol-9-yl; 2,7-di(tertiary-butyl)-carbazol-9-yl; 2,7-di(tertiary-octyl)-carbazol-9-yl; 2,7-diphenylcarbazol-9-yl; or 2,7-bis(2,4,6-trimethylphenyl)-carbazol-9-yl.

In one embodiment, for Formula 1, $R^{5c}=R^{5d}$.

In one embodiment, for Formula 1, each Z is —O— (oxygen atom).

In one embodiment, for Formula 1, M is selected from Zr or Hf. In a further embodiment, M is Zr.

In one embodiment, for Formula 1, n is 2, and each X is independently an alkyl.

In one embodiment, for Formula 1, n is 2, and each X is independently a (C1-C7)alkyl, further a (C1-C3)alkyl, and further each X is methyl.

In one embodiment, for Formula 1, Y is selected from the following: —CHR—, —CRR'—, —CR$_2$—, —CH$_2$—, —SiR$_2$—, —SiRR'—, —GeR$_2$—, —NR—, —CHOR—, —N—NR$_2$, or —PR—, and wherein each R is independently an alkyl, and further a C1-C5 alkyl, or an aryl, and further a C5-C12 aryl, and wherein each R' is independently an alkyl, and further a C1-C5 alkyl, or an aryl, and further a C5-C12 aryl.

In one embodiment, for Formula 1, Y is selected from the following: —CHR—, —CRR'—, —CR$_2$—, —CH$_2$—, and wherein each R is independently an alkyl, and further a C1-C5 alkyl, and each R' is independently an alkyl, and further a C1-C5 alkyl. In a further embodiment, Y is selected from the following: —CHR—, or —CR$_2$—, and wherein each R is independently an alkyl, and further a C1-C5 alkyl, and further a C1-C3 alkyl, and further a C1 alkyl. In a further embodiment, Y is —CH$_2$—.

In one embodiment, for Formula 1, $R^{3a}$ or $R^{3b}$ are each independently selected from the following: a halogen (e.g., —F or —Cl), an amine (e.g., —N(alkyl)$_2$), an alkoxyl (e.g., —O(alkyl)), or an alkyl (e.g., C3-C5 alkyl).

In one embodiment, for Formula 1, $R^{7c}$ and $R^{7d}$ are each independently an alkyl, further a (C1-C20)alkyl, and further a (C1-C10)alkyl.

In one embodiment, for Formula 1, $R^{1a}$, $R^{2a}$, $R^{4a}$, $R^{1b}$, $R^{2b}$, $R^{4b}$, $R^{6c}$, $R^{8c}$, $R^{6d}$ and $R^{8d}$ are each hydrogen.

In one embodiment, for Formula 1, Formula 1 is selected from the following structures a) through ee):

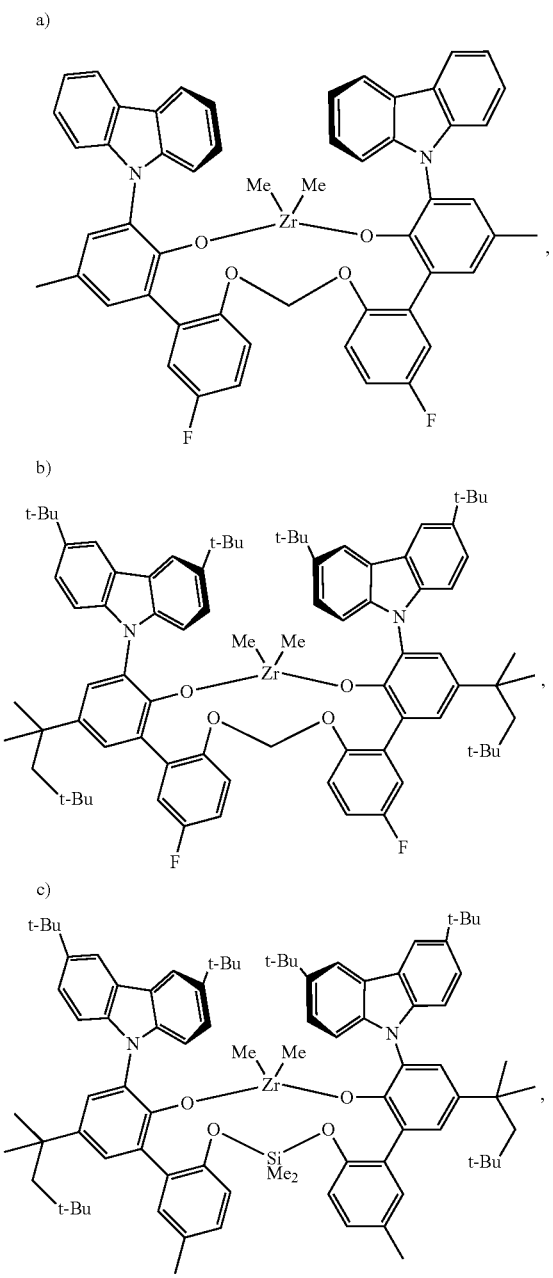

d)
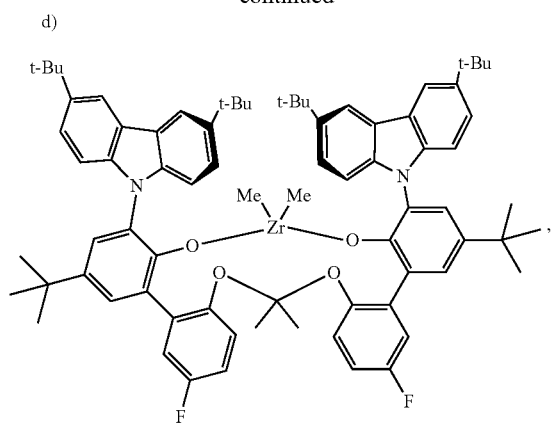
e)
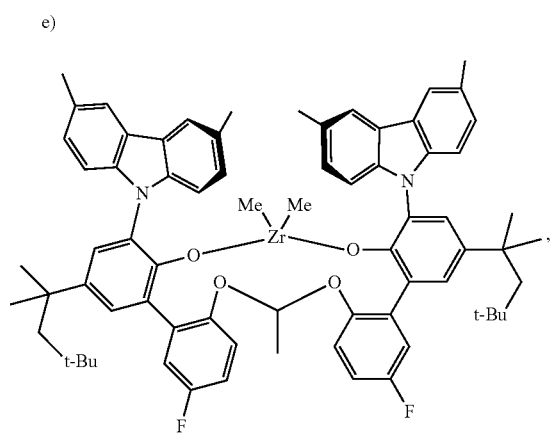
f)
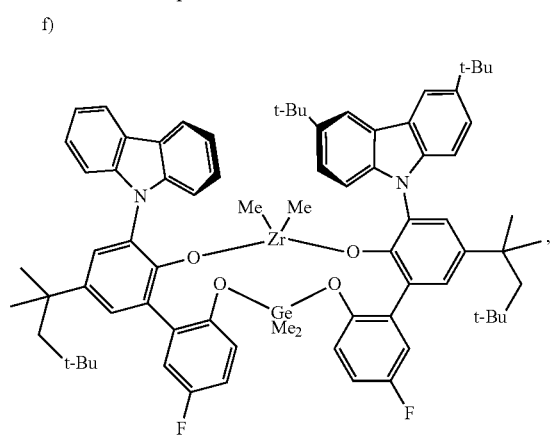
g)
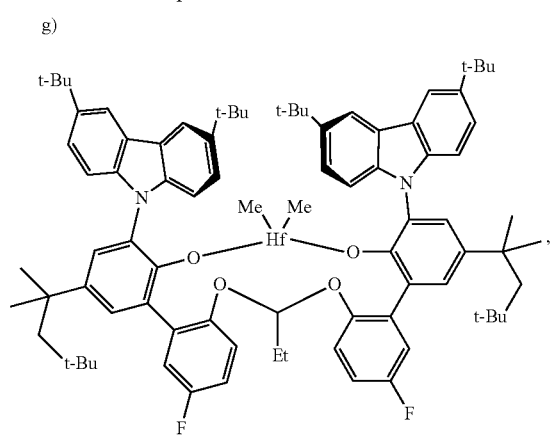
h)
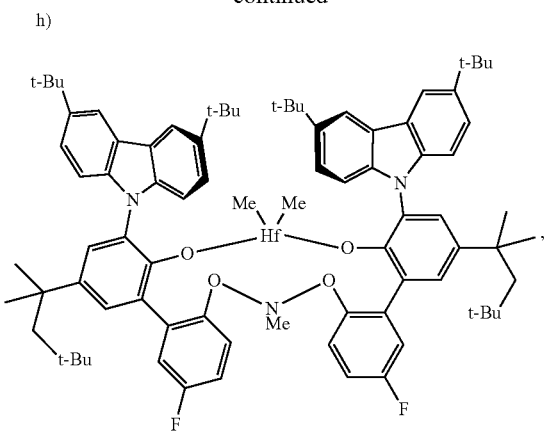
i)
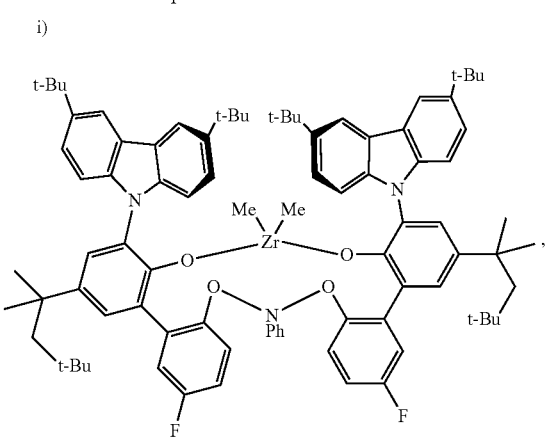
j)
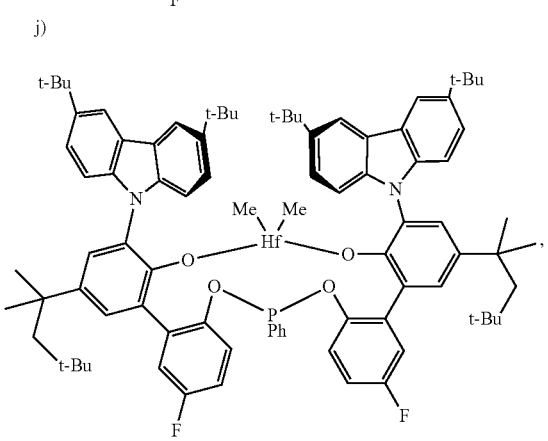
k)
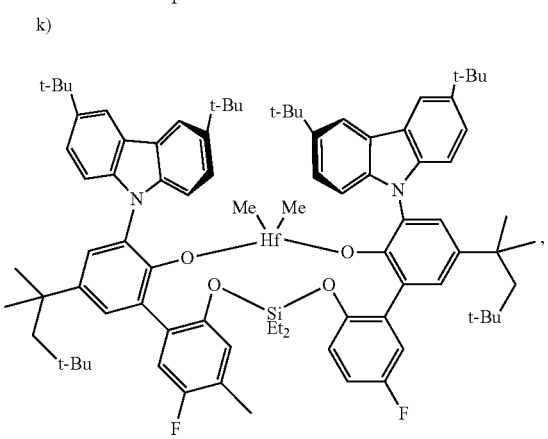

l)
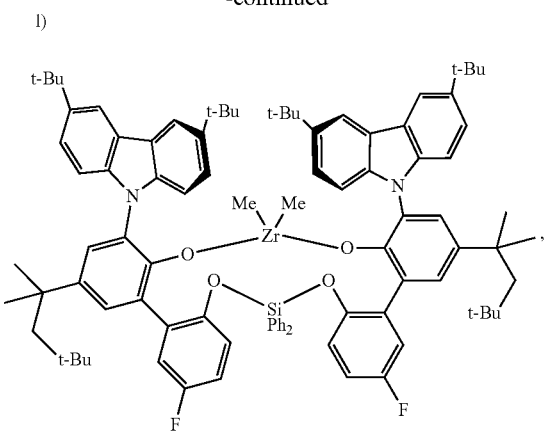
m)
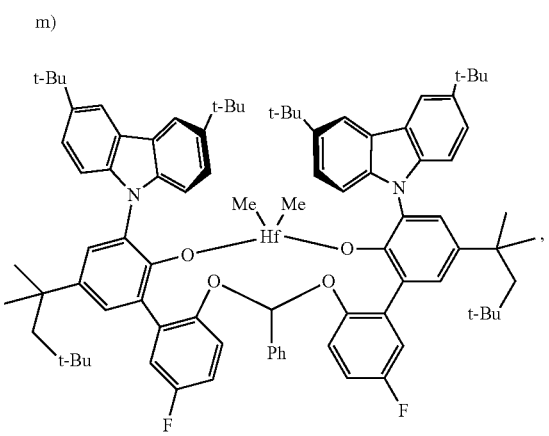
n)
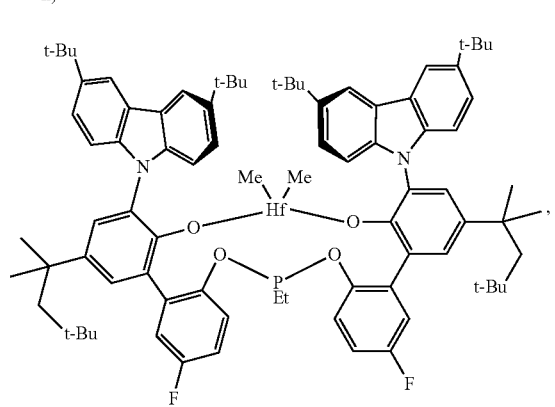
o)
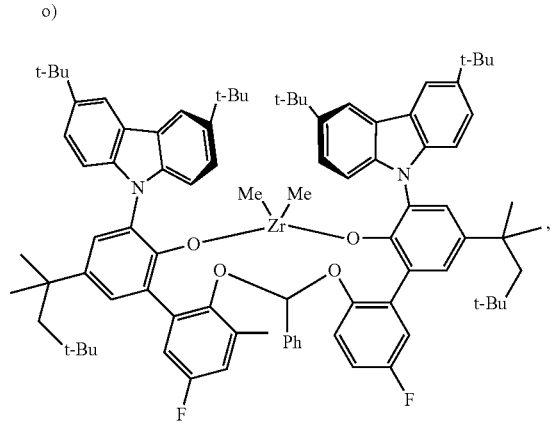
p)
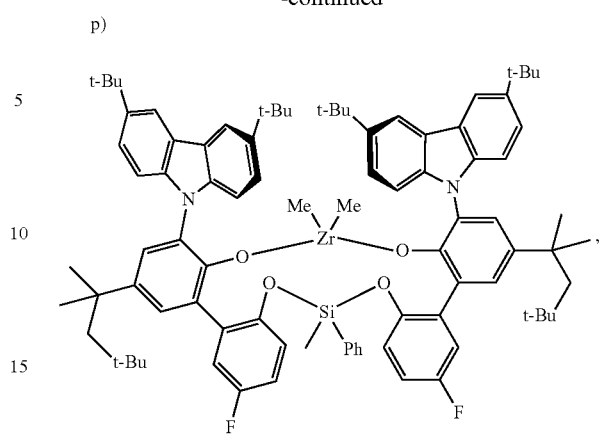
q)
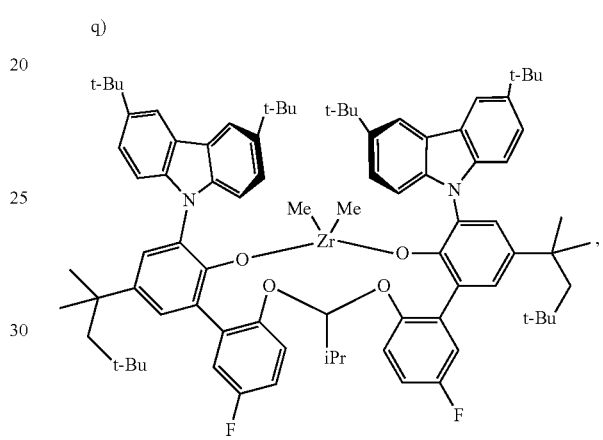
r)
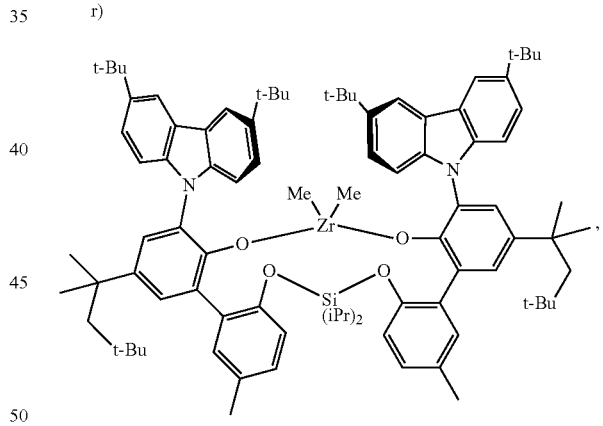
s)
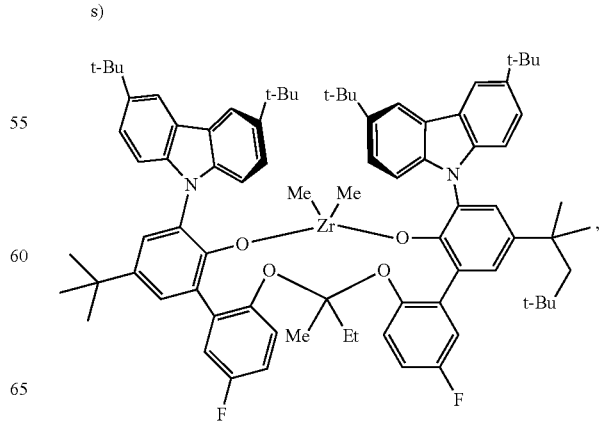

-continued
t)
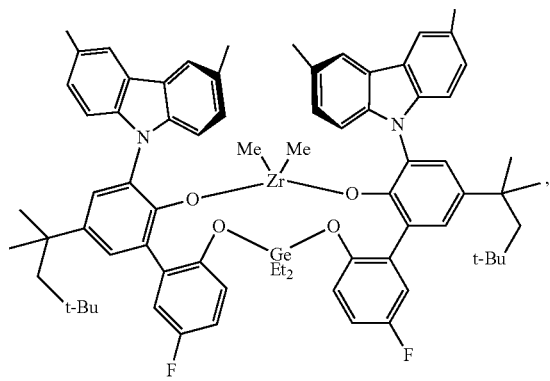
u)
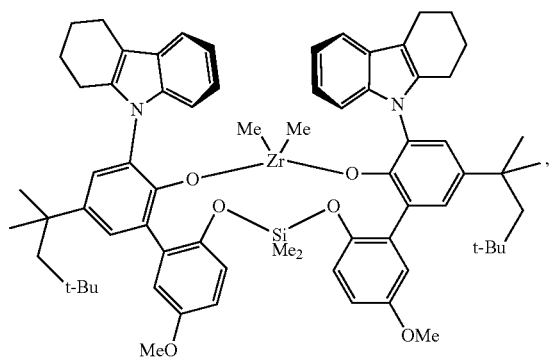
v)
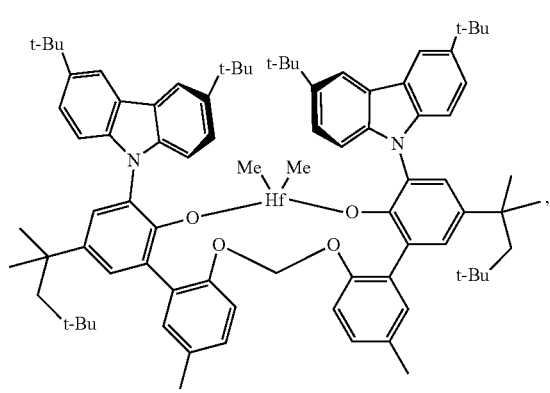
w)
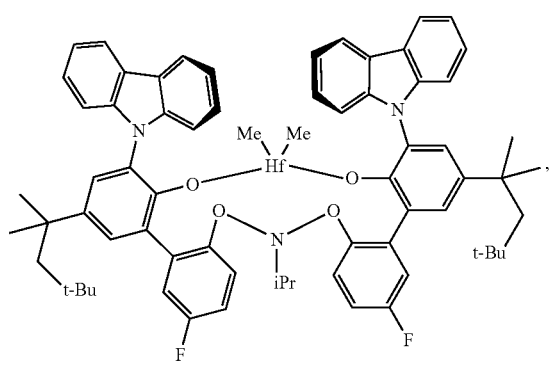
-continued
x)
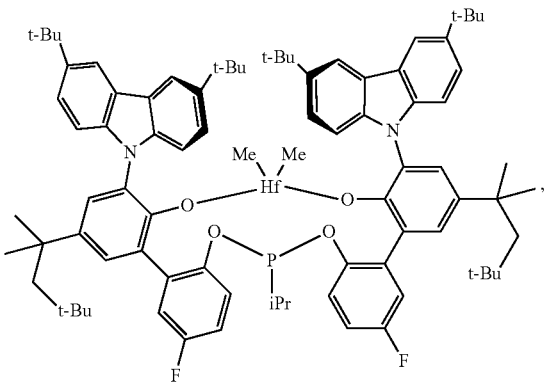
y)
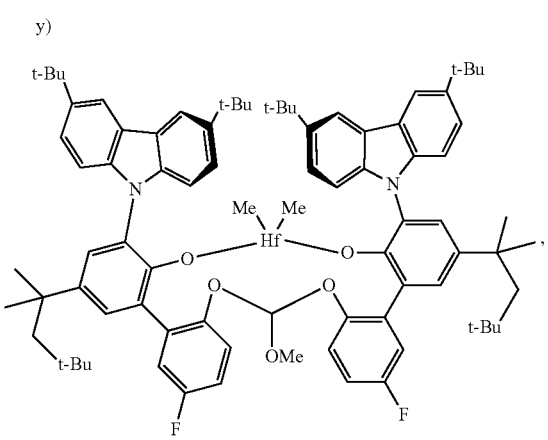
z)
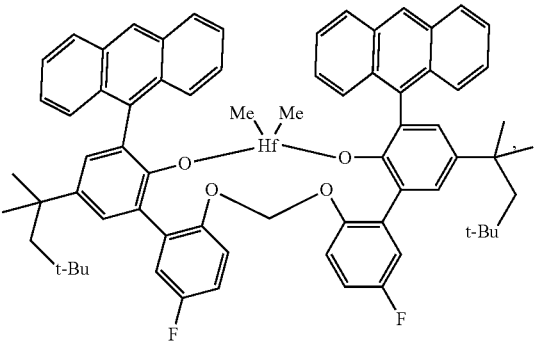
aa)
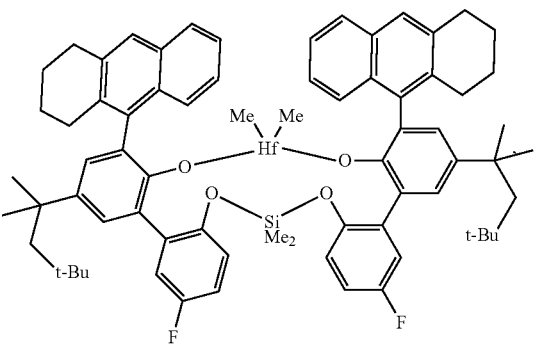

-continued bb)

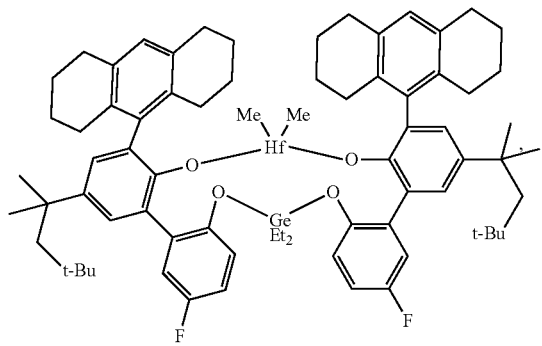

cc)

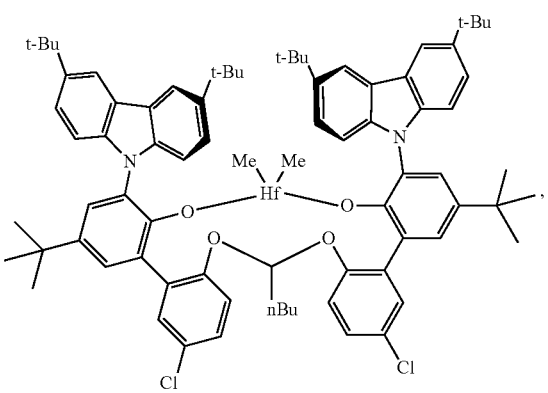

dd)

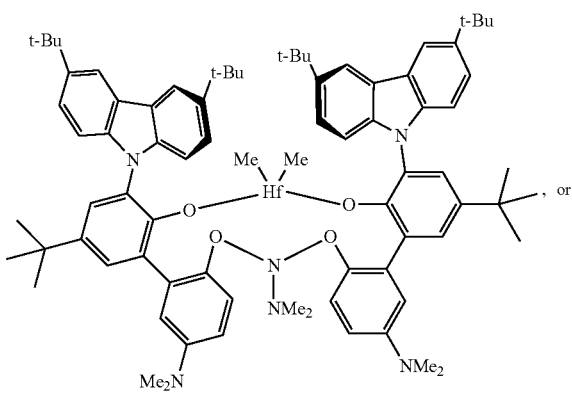

ee)

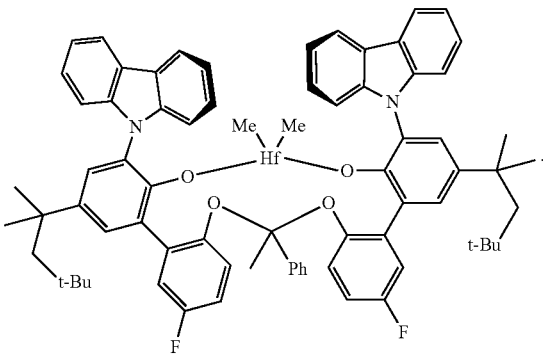

For each structure a) through ee), only one of the oxygen atoms in the $Z_1$ and $Z_2$ positions is dative covalent (coordinate) to the metal (Zr or Hf).

In one embodiment, Formula 1 is selected from the following structures a) through e); each as shown above.

In one embodiment, Formula 1 is selected from the following structures a) or b); each as shown above.

The invention also provides a process to form an ethylene-based polymer, said process comprising polymerizing a mixture comprising ethylene, and optionally at least one comonomer, in the presence of at least one inventive molecular transition metal complex as described herein.

In one embodiment, the inventive process is run at a polymerization temperature greater than, or equal to, 140° C., further greater than, or equal to, 150° C., further greater than, or equal to, 160° C., further greater than, or equal to, 170° C.

In one embodiment, the inventive process is run at a polymerization temperature less than, or equal to, 250° C., further less than, or equal to, 240° C., further less than, or equal to, 230° C., further less than, or equal to, 220° C.

In one embodiment, the inventive process is run in a solution polymerization, and further a continuous solution polymerization.

In one embodiment, the inventive process is run, using from 2.0 to 3.0 kg/hr ethylene, and less than, or equal to, 100 mL/min, further less than, or equal to, 90 mL/min, further less than, or equal to, 80 mL/min, hydrogen.

In one embodiment, the inventive process is run, using from 2.0 to 3.0 kg/hr ethylene, and less than, or equal to, 70 mL/min, further less than, or equal to, 60 mL/min, further less than, or equal to, 50 mL/min, hydrogen.

In one embodiment, the polymerization takes place in the presence of at least one inventive transition metal complex, and optionally one or more other catalyst systems, in one or more polymerization reactors, connected in parallel, series, or combinations thereof.

The invention also provides an ethylene-based polymer formed from an inventive process as described herein.

In one embodiment, the ethylene-based polymer is an ethylene/α-olefin interpolymer, and further an ethylene/α-olefin copolymer. Preferred α-olefins include, but are not limited to, C3-C20 α-olefins, and further C3-C10 α-olefins. More preferred α-olefins include propylene, 1-butene, 1-pentene, 1-hexene, 1-heptene and 1-octene, and further include propylene, 1-butene, 1-hexene and 1-octene, and further 1-butene, 1-hexene and 1-octene, and further 1-butene and 1-octene.

In one embodiment, the ethylene-based polymer has a weight average molecular weight ($M_w$) from 200 to 5,000 g/mole, further from 300 to 2,000, further from 400 to 1,000 g/mole.

In one embodiment, the ethylene-based polymer has a molecular weight distribution (MWD) from 1.1 to 3.0, further from 1.3 to 2.5, further from 1.5 to 2.0.

In one embodiment, the ethylene-based polymer has a melting temperature (Tm) from 50° C. to 100° C., further from 60° C. to 90° C., further from 70° C. to 80° C.

The invention also provides a composition comprising an inventive ethylene-based polymer. In a further embodiment, the composition further comprises one or more additives.

The invention also provides an article comprising at least one component formed from an inventive composition.

An inventive ethylene-based polymer may comprise a combination of two or more embodiments described herein.

An inventive composition may comprise a combination of two or more embodiments described herein.

An inventive article may comprise a combination of two or more embodiments described herein.

An inventive process may comprise a combination of two or more embodiments described herein.

The molecular transition metal complex of Formula 1 may comprise a combination of two or more embodiments described herein.

The present invention employs one or more transition metal complexes of Formula 1, which is described herein using conventional chemical group terminology. When used to describe certain carbon atom-containing chemical groups (e.g., $(C_1-C_{40})$alkyl), the parenthetical expression $(C_1-C_{40})$ can be represented by the form "$(C_v-C_w)$," which means that the unsubstituted version of the chemical group comprises from a number v carbon atoms to a number w carbon atoms, wherein each v and w independently is an integer as described for the chemical group.

The term "substituted," as used herein, with respect to a chemical compound, refers to a substituent that comprises at least one heteroatom (for example, O, S, N, P, etc.). Substituents include, but are not limited to, the $R^S$ substituents as follows: a halogen atom, a polyfluoro substituent, a perfluoro substituent, $F_3C-$, $FCH_2O-$, $F_2HCO-$, $F_3CO-$, $(R^C)_3Si-$, $(R^C)_3Ge-$, $(R^C)O-$, $(R^C)S-$, $(R^C)S(O)-$, $(R^C)S(O)_2-$, $(R^C)_2P-$, $(R^C)_2N-$, $(R^C)_2C=N-$, $NC-$, $(R^C)C(O)O-$, $(R^C)OC(O)-$, $(R^C)C(O)N(R^C)-$, and $(R^C)_2NC(O)-$; wherein each $R^C$ is independently a substituted or unsubstituted $(C_1-C_{30})$hydrocarbyl, or a substituted or unsubstituted $(C_1-C_{30})$ heterohydrocarbyl.

The term "unsubstituted," as used herein, with respect to a chemical compound, refers to the lack of a substituent that comprises at least one heteroatom (for example, O, S, N, P, etc.).

The term "hydrocarbyl," as used herein, refers to a monovalent (monoradical or radical) chemical group containing only hydrogen and carbon atoms.

The term "substituted hydrocarbyl," as used herein, refers to a hydrocarbyl, in which at least one hydrogen atom is substituted with a substituent that comprises at least one heteroatom.

The term "heterohydrocarbyl," as used herein, refers to a hydrocarbyl, in which at least one carbon atom, or CH group, or $CH_2$ group, is substituted with a heteroatom or a chemical group containing at least one heteroatom. Heteroatoms include, but are not limited to, O, N, P and S.

The term "substituted heterohydrocarbyl," as used herein, refers to a heterohydrocarbyl in which at least one hydrogen atom is substituted with a substituent that comprises at least one heteroatom.

The term "hydrocarbylene," as used herein, refers to a divalent (diradical) chemical group containing only hydrogen and carbon atoms.

The term "substituted hydrocarbylene," as used herein, refers to a hydrocarbylene, in which at least one hydrogen atom is substituted with a substituent that comprises at least one heteroatom.

The term "heterohydrocarbylene," as used herein, refers to a hydrocarbylene, in which at least one carbon atom, or CH group, or $CH_2$ group, is substituted with a heteroatom or a chemical group containing at least one heteroatom. Heteroatoms include, but are not limited to, O, N, P and S.

The term "substituted heterohydrocarbylene," as used herein, refers to a heterohydrocarbylene, in which at least one hydrogen atom is substituted with a substituent that comprises at least one heteroatom.

As used herein, the term "$(C_1-C_{40})$hydrocarbyl" refers to hydrocarbon radical of from 1 to 40 carbon atoms. Each hydrocarbon radical, independently, may be aromatic (6 carbon atoms or more) or non-aromatic, saturated or unsaturated, straight chain or branched chain, cyclic (including mono and polycyclic, fused and non-fused polycyclic, including bicyclic; 3 carbon atoms or more) or acyclic, or a combination of two or more thereof; and each hydrocarbon radical independently is the same as, or different from, another hydrocarbon radical, respectively.

Preferably, a $(C_1-C_{40})$hydrocarbyl is independently a $(C_1-C_{40})$alkyl, or a $(C_3-C_{40})$cycloalkyl. More preferably, each of the aforementioned $(C_1-C_{40})$hydrocarbyl groups independently has a maximum of 20 carbon atoms (i.e., $(C_1-C_{20})$hydrocarbyl), and still more preferably a maximum of 12 carbon atoms.

As used herein, the term "$(C_1-C_{40})$hydrocarbylene" refers to a hydrocarbon diradical of from 1 to 40 carbon atoms. Each hydrocarbon diradical, independently, may be aromatic (6 carbon atoms or more) or non-aromatic, saturated or unsaturated, straight chain or branched chain, cyclic (including mono- and poly-cyclic, fused and non-fused polycyclic, including bicyclic; 3 carbon atoms or more) or acyclic, or a combination of two or more thereof; and each hydrocarbon diradical independently is the same as, or different from, another hydrocarbon diradical, respectively.

Preferably, a $(C_1-C_{40})$hydrocarbylene, independently, is a $(C_3-C_{20})$cycloalkyl-$(C_1-C_{20})$alkylene, $(C_6-C_{40})$aryl, or $(C_6-C_{20})$aryl-$(C_1-C_{20})$alkylene. More preferably, each of the aforementioned $(C_1-C_{40})$hydrocarbylene groups independently has a maximum of 20 carbon atoms (i.e., $(C_1-C_{20})$hydrocarbyl), and still more preferably a maximum of 12 carbon atoms.

The term "$(C_1-C_{40})$heterohydrocarbyl" refers to a heterohydrocarbon radical of from 1 to 40 carbon atoms. Each heterohydrocarbyl, independently, has one or more heteroatoms, for example, O; S; S(O); $S(O)_2$; $Si(R^C)_2$; $Ge(R^C)_2$; $P(R^P)$; and $N(R^N)$, wherein independently each $R^C$ is unsubstituted $(C_1-C_{18})$hydrocarbyl, each $R^P$ is unsubstituted $(C_1-C_{18})$hydrocarbyl; and each $R^N$ is unsubstituted $(C_1-C_{18})$hydrocarbyl or absent (e.g., absent when N comprises $-N=$ or tri-carbon substituted N). The heterohydrocarbon radical is on a carbon atom or heteroatom thereof, although preferably is on a carbon atom when bonded to a heteroatom in Formula (I) or to a heteroatom of another heterohydrocarbyl. Each $(C_1-C_{40})$heterohydrocarbyl independently may be saturated or unsaturated, straight chain or branched chain, cyclic (including mono- and poly-cyclic, fused and non-fused polycyclic) or acyclic, or a combination of two or more thereof; and each is respectively the same as or different from another.

The term "$(C_1-C_{40})$heterohydrocarbylene refers to a heterohydrocarbon diradical of from 1 to 40 carbon atoms. Each heterohydrocarbylene, independently, has one or more heteroatoms, for example, O; S; S(O); $S(O)_2$; $Si(R^C)_2$; $Ge(R^C)_2$; $P(R^P)$; and $N(R^N)$, wherein independently each $R^C$ is unsubstituted $(C_1-C_{18})$hydrocarbyl, each $R^P$ is unsubstituted $(C_1-C_{18})$hydrocarbyl; and each $R^N$ is unsubstituted $(C_1-C_{18})$hydrocarbyl or absent (e.g., absent when N comprises $-N=$ or tri-carbon substituted N). The heterohydrocarbon radical and each of the heterohydrocarbon diradicals independently is on a carbon atom or heteroatom thereof, although preferably is on a carbon atom when bonded to a heteroatom in Formula (I) or to a heteroatom of another heterohydrocarbyl or heterohydrocarbylene.

Preferably, the $(C_1-C_{40})$heterohydrocarbyl independently is $(C_1-C_{40})$heteroalkyl, $(C_1-C_{40})$hydrocarbyl-O—, $(C_1-C_{40})$hydrocarbyl-S—, $(C_1-C_{40})$hydrocarbyl-S(O)—, $(C_1-C_{40})$hydrocarbyl-$S(O)_2$—, $(C_1-C_{40})$hydrocarbyl-$Si(R^C)_2$—, $(C_1-$ $C_{40}$)hydrocarbyl-Ge($R^C$)$_2$—, ($C_1$-$C_{40}$)hydrocarbyl-N($R^N$)—, ($C_1$-$C_{40}$)hydrocarbyl-P($R^P$)—, ($C_2$-$C_{40}$) heterocycloalkyl.

Preferably, the ($C_1$-$C_{40}$)heterohydrocarbylene independently is ($C_2$-$C_{19}$)hetero-cycloalkyl-($C_1$-$C_{20}$)alkylene, ($C_3$-$C_{20}$)cycloalkyl-($C_1$-$C_{19}$)heteroalkylene, ($C_2$-$C_{19}$)heterocycloalkyl-($C_1$-$C_{20}$)heteroalkylene, ($C_1$-$C_{40}$)heteroarylene, ($C_1$-$C_{19}$)heteroaryl-($C_1$-$C_{20}$)alkylene, ($C_6$-$C_{20}$)aryl-($C_1$-$C_{19}$)heteroalkylene, or ($C_1$-$C_{19}$)heteroaryl-($C_1$-$C_{20}$)heteroalkylene.

The term "halogen atom" refers to a fluorine atom radical (F), chlorine atom radical (Cl), bromine atom radical (Br), or iodine atom radical (I). Preferably each halogen atom independently is a Br, F, or Cl radical, and more preferably a F or Cl radical, and more preferably a F radical.

Preferably, there are no O—O, S—S, or O—S bonds, other than O—S bonds in an S(O) or S(O)$_2$ diradical functional group, in the transition metal complex of Formula 1. More preferably, there are no O—O, N—N, P—P, N—P, S—S, or O—S bonds, other than O—S bonds in an S(O) or S(O)$_2$ diradical functional group, in the transition metal complex of Formula 1.

The term "saturated" means lacking double bonds or triple bonds, for example, carbon-carbon double bonds, carbon-carbon triple bonds, and (in heteroatom-containing groups) carbon-nitrogen, carbon-phosphorous, and carbon-silicon multiple bonds.

The term "unsaturated" means containing one or more double bonds and/or triple bonds, for example, carbon-carbon double bonds, carbon-carbon triple bonds, and (in heteroatom-containing groups) carbon-nitrogen, carbon-phosphorous, and/or carbon-silicon multiple bonds.

The metal M of Formula 1 is preferably selected from zirconium (Zr), hafnium (Hf), and titanium (Ti), and preferably from Zr or Hf, and more preferably Zr. In some embodiments, M is in a formal oxidation state of +2, +3, or +4. In some embodiments, n is 0, 1, 2, or 3. Each X independently is a monodentate ligand that is neutral, monoanionic, or dianionic; or two Xs are taken together to form a bidentate ligand that is neutral, monoanionic, or dianionic. X and n are chosen, in such a way, that the metal-ligand complex of Formula 1 is, overall, neutral. In some embodiments each X, independently, is the monodentate ligand. In one embodiment, when there are two or more X monodentate ligands, each X is the same. In some embodiments the monodentate ligand is the monoanionic ligand. The monoanionic ligand has a net formal oxidation state of −1. Each monoanionic ligand may independently be hydride, ($C_1$-$C_{40}$)hydrocarbyl carbanion, ($C_1$-$C_{40}$)heterohydrocarbyl carbanion, halide, nitrate, carbonate, phosphate, sulfate, HC(O)O$^-$, ($C_1$-$C_{40}$)hydrocarbylC(O)O$^-$, HC(O)N(H)$^-$, ($C_1$-$C_{40}$)hydrocarbylC(O)N(H)$^-$, ($C_1$-$C_{40}$)hydrocarbylC(O)N(($C_1$-$C_{20}$)hydrocarbyl)$^-$, $R^K R^L B^-$, $R^K R^L N^-$, $R^K O^-$, $R^K S^-$, $R^K R^L P^-$, or $R^M R^K R^L Si^-$, wherein each $R^K$, $R^L$, and $R^M$ independently is hydrogen, ($C_1$-$C_{40}$)hydrocarbyl, or ($C_1$-$C_{40}$)heterohydrocarbyl, or $R^K$ and $R^L$ are taken together to form a ($C_2$-$C_{40}$)hydrocarbylene or ($C_1$-$C_{40}$)heterohydrocarbylene and $R^M$ is as defined above.

In some embodiments, at least one monodentate ligand X independently is a neutral ligand. In one embodiment, the neutral ligand is a neutral Lewis base group that is $R^X$N-$R^K R^L$, $R^K O R^L$, $R^K S R^L$, or $R^X P R^K R^L$, wherein each $R^X$ independently is hydrogen, ($C_1$-$C_{40}$)hydro-carbyl, [($C_1$-$C_{10}$)hydrocarbyl]$_3$Si, [($C_1$-$C_{10}$)hydrocarbyl]$_3$Si($C_1$-$C_{10}$)hydrocarbyl, or ($C_1$-$C_{40}$)heterohydrocarbyl and each $R^K$ and $R^L$ independently is as defined above.

In some embodiments, each X is a monodentate ligand that independently is a halogen atom, unsubstituted ($C_1$-$C_{20}$) hydrocarbyl, unsubstituted ($C_1$-$C_{20}$)hydrocarbylC(O)O—, or $R^K R^L$N— wherein each of $R^K$ and $R^L$, independently, is an unsubstituted ($C_1$-$C_{20}$)hydrocarbyl. In some embodiments each monodentate ligand X is a chlorine atom, ($C_1$-$C_{10}$)hydrocarbyl (e.g., ($C_1$-$C_6$)alkyl or benzyl), unsubstituted ($C_1$-$C_{10}$)hydrocarbylC(O)O—, or $R^K R^L$N— wherein each of $R^K$ and $R^L$ independently is an unsubstituted ($C_1$-$C_{10}$)hydrocarbyl.

In some embodiments, there are at least two X, and the two X are taken together to form the bidentate ligand. In some embodiments the bidentate ligand is a neutral bidentate ligand. In one embodiment, the neutral bidentate ligand is a diene of formula ($R^D$)$_2$C=C($R^D$)—C($R^D$)=C($R^D$)$_2$, wherein each $R^D$, independently, is H, unsubstituted ($C_1$-$C_6$)alkyl, phenyl, or naphthyl. In some embodiments, the bidentate ligand is a monoanionic-mono(Lewis base) ligand. The monoanionic-mono(Lewis base) ligand may be a 1,3-dionate of formula (D): $R^E$—C(O$^-$)=CH—C(=O)—$R^E$ (D), wherein each $R^E$, independently, is H, unsubstituted ($C_1$-$C_6$)alkyl, phenyl, or naphthyl. In some embodiments, the bidentate ligand is a dianionic ligand. The dianionic ligand has a net formal oxidation state of −2. In one embodiment, each dianionic ligand independently is carbonate, oxalate (i.e., $^-O_2CC(O)O^-$), ($C_2$-$C_{40}$)hydrocarbylene dicarbanion, ($C_1$-$C_{40}$)heterohydrocarbylene dicarbanion, phosphate, or sulfate.

As previously mentioned, number and charge (neutral, monoanionic, dianionic) of X are selected, depending on the formal oxidation state of M, such that the transition metal complex of Formula 1 is overall, neutral.

In some embodiments, each X is the same, wherein each X is methyl; ethyl; 1-propyl; 2-propyl; 1-butyl; 2,2,-dimethylpropyl; trimethylsilylmethyl; phenyl; benzyl; or chloro. In some embodiments, n is 2, and each X is the same.

In some embodiments, at least two X are different. In some embodiments, n is 2, and each X is a different one of methyl; ethyl; 1-propyl; 2-propyl; 1-butyl; 2,2,-dimethylpropyl; trimethylsilylmethyl; phenyl; benzyl; or chloro.

The integer n indicates the number of X groups. In one embodiment, n is 2 or 3, and at least two X, independently, are monoanionic monodentate ligands, and a third X, if present, is a neutral monodentate ligand. In some embodiments n is 2, and two X are taken together to form a bidentate ligand. In some embodiments, the bidentate ligand is 2,2-dimethyl-2-silapropane-1,3-diyl or 1,3-butadiene.

In one embodiment, each Z independently is —O—, —S—, —N[($C_1$-$C_{40}$)hydrocarbyl]-, or —P[($C_1$-$C_{40}$)hydrocarbyl]-. In some embodiments, each Z is different. In some embodiments, one Z is —O—, and one Z is —N[($C_1$-$C_{40}$)hydrocarbyl]- (e.g., —N(CH$_3$)—). In some embodiments, one Z is —O—, and one Z is —S—. In some embodiments, one Z is —S—, and one Z is —N[($C_1$-$C_{40}$)hydro-carbyl]- (e.g., —N(CH$_3$)—). In some embodiments, each Z is the same. In some embodiments, each Z is —O—. In some embodiments, each Z is —S—. In some embodiments, each Z is —N[($C_1$-$C_{40}$)-hydrocarbyl]- (e.g., —N(CH$_3$)—). In some embodiments, at least one, and in some embodiments each Z, is —P[($C_1$-$C_{40}$)hydrocarbyl]- (e.g., —P(CH$_3$)—).

Polymerization

In order to prepare the homopolymers, interpolymers, or copolymers of the invention, ethylene and/or the selected alpha-olefin monomer(s) is/are fed into a suitable reactor, for batch, semi-continuous, or continuous production, wherein such monomer(s) will come into contact with the catalyst. In the case of preparation of a copolymer, it is noted that the ethylene/alpha-olefin reactivity ratio is distinct for any given catalyst, and provides a methodology to determine the amount of alpha-olefin that will be required to attain a targeted copolymer composition. Reactivity ratios may be determined using well-known theoretical techniques, or empirically derived from actual polymerization data. Suitable theoretical techniques are disclosed, for example, in B. G. Kyle, *Chemical and Process Thermodynamics*, $3^{rd}$ ed., Prentice-Hall (Englewood Cliffs, N J 1999) and in G. Soave, "Redlich-Kwong-Soave (RKS) Equation of State," *Chemical Engineering Science*, 1972, vol. 27, pp 1197-1203. Commercially available software programs may be used to assist in deriving reactivity ratios from experimentally derived data. One example of such software is Aspen Plus from Aspen Technology, Inc., Ten Canal Park, Cambridge, Mass. 02141-2201, USA. In one embodiment, the target amount of alpha-olefin in a copolymer range from 1 to 30 mole percent (mol %); more preferably from 1 to 25 mol %; and still more preferably from 1 to 20 mol %, based on the total moles of polymerized monomers.

The transition metal complex of Formula 1 is rendered catalytically active by contacting it to, or combining it with, the activating cocatalyst, or by using an activating technique, such as those that are known in the art for use with metal-based olefin polymerization reactions. Many activating cocatalysts and activating techniques have been previously taught, with respect to different metal-ligand complexes, in the following patent references: U.S. Pat. Nos. 5,064,802; 5,153,157; 5,296,433; 5,321,106; 5,350,723; 5,425,872; 5,625,087; 5,721,185; 5,783,512; 5,883,204; 5,919,983; 6,696,379; and 7,163,907. Examples of suitable hydrocarbyloxides are disclosed in U.S. Pat. No. 5,296,433. Examples of suitable Bronsted acid salts for addition polymerization catalysts are disclosed in U.S. Pat. Nos. 5,064,802; 5,919,983; 5,783,512. Examples of suitable salts of a cationic oxidizing agent and a non-coordinating, compatible anion as activating cocatalysts for addition polymerization catalysts are disclosed in U.S. Pat. No. 5,321,106. Examples of suitable carbenium salts as activating cocatalysts for addition polymerization catalysts are disclosed in U.S. Pat. No. 5,350,723. Examples of suitable silylium salts as activating cocatalysts for addition polymerization catalysts are disclosed in U.S. Pat. No. 5,625,087. Examples of suitable complexes of alcohols, mercaptans, silanols, and oximes with tris(pentafluorophenyl)borane are disclosed in U.S. Pat. No. 5,296,433. Some of these catalysts are also described in a portion of U.S. Pat. No. 6,515,155, beginning at column 50, at line 39, and going through column 56, at line 55, only the portion of which is incorporated by reference herein.

In some embodiments, the transition metal complex of Formula 1, may be activated to form an active catalyst composition, by combination with one or more cocatalysts, such as a cation-forming cocatalyst, a strong Lewis acid, or a combination thereof. Suitable cocatalysts include polymeric or oligomeric aluminoxanes, especially methyl aluminoxane, as well as inert, compatible, noncoordinating, ion-forming compounds. Exemplary suitable cocatalysts include, but are not limited to modified methyl aluminoxane (MMAO), triethyl aluminum (TEA), tris-pentafluorophenyl borane, bis-hydrogenatedtallowalkylmethylammonium tetrakis-pentafluoro-phenylborate, methylbis(octadecyl)ammonium tetrakis(pentafluorophenyl)borate, and any combination thereof. In one embodiment, the cocatalyst is selected from tris-pentafluorophenyl borane, modified methaluminoxane, bis-hydrogenatedtallowalkyl-methylammonium tetrakis-pentafluorophenylborate, and combinations thereof.

In some embodiments, one or more of the foregoing activating cocatalysts are used in combination with each other. For example, a combination of a tri(($C_1$-$C_4$)hydrocarbyl)-aluminum, tri(($C_1$-$C_4$)hydrocarbyl)borane, or an ammonium borate with an oligomeric or polymeric alumoxane compound.

The ratio of total number of moles of one or more transition metal complexes of Formula 1 to total number of moles of one or more of the activating cocatalysts is from 1:10,000 to 100:1. In some embodiments, the ratio is at least 1:5000, in some other embodiments, at least 1:1000 or 1:100; and 10:1 or less, and in some other embodiments, 1:1 or less. When an alumoxane, alone, is used as the activating cocatalyst, preferably the number of moles of the alumoxane employed is at least 10 times, further at least 40 times, further at least 100 times the number of moles of the transition metal complex of Formula 1. When tris(pentafluorophenyl)-borane, alone, is used as the activating cocatalyst, in some other embodiments, the number of moles of the tris(pentafluoro-phenyl)borane employed, to the total number of moles of one or more transition metal complexes of Formula 1, is from 0.5:1 to 10:1, in some other embodiments, from 1:1 to 6:1, in some other embodiments, from 1:1 to 5:1. The remaining activating cocatalysts are generally employed in approximately mole quantities equal to the total mole quantities of one or more transition metal complexes of Formula 1.

A variety of homopolymerization or copolymerization conditions, and combinations thereof, may be employed, according to the starting materials, nature of the reaction (batch, semi-continuous, or continuous), apparatus set-up, desired products, and so forth. However, in general, suitable polymers, interpolymers, or copolymers of the invention, may be produced using one or more of the specified transition metal complexes of Formula 1, at a temperatures preferably from 150° C. to 250° C., further from 160° C. to 240° C., further from 170° C. to 230° C. A reaction time may range from 10 minutes to 300 minutes. Other parameters, such as pressure, may be controlled, and varied, according to the desires and needs of the practitioner. It is usually preferred to carry out the process as a continuous process, further using at least one continuous stirred-tank reactor (CSTR) or other suitable vessel(s); and preferably a continuous solution process, further using at least one continuous stirred-tank reactor (CSTR) or other suitable vessel(s).

Ethylene-Based Polymers

The ethylene-based polymer may be an ethylene homopolymer, an ethylene-based interpolymer, or an ethylene-based copolymer.

In one embodiment, the ethylene-based polymer is an ethylene/α-olefin interpolymer, and further an ethylene/α-olefin copolymer. Preferred α-olefins include, but are not limited to, C3-C20 α-olefins, further C3-C12 α-olefins, and further C3-C10 α-olefins. More preferred α-olefins include propylene, 1-butene, 1-pentene, 1-hexene, 1-heptene and 1-octene, and more further include propylene, 1-butene, 1-hexene and 1-octene, further 1-butene, 1-hexene and 1-octene, further 1-butene and 1-octene.

In one embodiment, the ethylene-based polymer has a melt viscosity less than, or equal to, 5,000 cP, further less than, or equal to, 4,000 cP, further less than, or equal to, 3,000 cP, further less than, or equal to, 2,000 cP, further less than, or equal to, 1,000 cP, at 350° F. (177° C.). In a further embodiment, the ethylene-based polymer is an ethylene/α-olefin interpolymer, and further an ethylene/α-olefin copolymer. Suitable α-olefins are described above.

In one embodiment, the ethylene-based polymer has a melt viscosity greater than, or equal to, 20 cP, further greater than, or equal to, 50 cP, more further greater than, or equal to, 100 cP, at 350° F. (177° C.). In a further embodiment, the ethylene-based polymer is an ethylene/α-olefin interpolymer, and further an ethylene/α-olefin copolymer. Suitable α-olefins are described above.

In one embodiment, the ethylene-based polymer has a weight average molecular weight less than, or equal to, 10,000 g/mole, and further less than, or equal to, 5,000 g/mole, and further less than, or equal to, 2,000 g/mole, and more further less than, or equal to, 1,000 g/mole. In a further embodiment, the ethylene-based polymer is an ethylene/α-olefin interpolymer, and further an ethylene/α-olefin copolymer. Suitable α-olefins are described above.

In one embodiment, the ethylene-based polymer has a weight average molecular weight ($M_w$) from 100 to 10,000 g/mole, further from 200 to 5,000 g/mole, further from 300 to 2,000, further from 400 to 1,000 g/mole. In a further embodiment, the ethylene-based polymer is an ethylene/α-olefin interpolymer, and further an ethylene/α-olefin copolymer. Suitable α-olefins are described above.

In one embodiment, the ethylene-based polymer has a molecular weight distribution (Mw/Mn) less than, or equal to, 3.0, and further less than, or equal to, 2.8, and further less than, or equal to, 2.5, and more further less than, or equal to, 2.0. Further the ethylene/α-olefin interpolymers have a molecular weight distribution from 1.1 to 3.0, and further from 1.3 to 2.5, and more further from 1.5 to 2.0. In a further embodiment, the ethylene-based polymer is an ethylene/α-olefin interpolymer, and further an ethylene/α-olefin copolymer. Suitable α-olefins are described above.

In one embodiment, the ethylene-based polymer has a melt index (I2 or MI), or calculated melt index (I2), greater than, or equal to, 500 g/10 min, further greater than, or equal to, 1000 g/10 min, and more further greater than, or equal to, 2000 g/10 min. In a further embodiment, the ethylene-based polymer is an ethylene/α-olefin interpolymer, and further an ethylene/α-olefin copolymer. Suitable α-olefins are described above.

In one embodiment, the ethylene-based polymer has a melting temperature (Tm) from 50° C. to 100° C., further from 60° C. to 90° C., further from 70° C. to 80° C. In a further embodiment, the ethylene-based polymer is an ethylene/α-olefin interpolymer, and further an ethylene/α-olefin copolymer. Suitable α-olefins are described above.

In one embodiment, the ethylene-based polymer has a percent crystallinity from 5 to 50 percent, further from 10 to 50 percent, and more further from 20 to 50 percent, as determined by DSC. In a further embodiment, the ethylene-based polymer is an ethylene/α-olefin interpolymer, and further an ethylene/α-olefin copolymer. Suitable α-olefins are described above.

In one embodiment, the ethylene-based polymer has a density greater than, or equal to, 0.855 g/cc, further greater than, or equal to, 0.860 g/cc, more further greater than, or equal to, 0.865 g/cc (1 cc=1 cm3). In a further embodiment, the ethylene-based polymer is an ethylene/α-olefin interpolymer, and further an ethylene/α-olefin copolymer. Suitable α-olefins are described above.

In one embodiment, the ethylene-based polymer has a density less than, or equal to, 0.900 g/cc, further less than, or equal to, 0.895 g/cc, more further less than, or equal to, 0.890 g/cc. In a further embodiment, the ethylene-based polymer is an ethylene/α-olefin interpolymer, and further an ethylene/α-olefin copolymer. Suitable α-olefins are described above.

In one embodiment, the ethylene/α-olefin interpolymer is a homogeneously branched linear interpolymer, and further a copolymer, or a homogeneous branched substantially linear interpolymer, and further a copolymer. Suitable α-olefins are described above.

In one embodiment, the ethylene/α-olefin interpolymer is a homogeneously branched linear interpolymer, and further a copolymer. Suitable α-olefins are described above.

In one embodiment, the ethylene/α-olefin interpolymer is a homogeneous branched substantially linear interpolymer, and further a copolymer. Suitable α-olefins are described above.

The terms "homogeneous" and "homogeneously-branched" are used in reference to an ethylene/α-olefin interpolymer, in which the α-olefin comonomer is randomly distributed within a given polymer molecule, and all of the polymer molecules have the same or substantially the same comonomer-to-ethylene ratio.

The homogeneously branched linear ethylene interpolymers are ethylene polymers, which lack long chain branching, but do have short chain branches, derived from the comonomer polymerized into the interpolymer, and which are homogeneously distributed, both within the same polymer chain, and between different polymer chains. These ethylene/α-olefin interpolymers have a linear polymer backbone, no measurable long chain branching, and a narrow molecular weight distribution. This class of polymers is disclosed, for example, by Elston in U.S. Pat. No. 3,645,992, and subsequent processes to produce such polymers, using bis-metallocene catalysts, have been developed, as shown, for example, in EP 0 129 368; EP 0 260 999; U.S. Pat. Nos. 4,701,432; 4,937,301; 4,935,397; 5,055,438; and WO 90/07526; each incorporated herein by reference. As discussed, the homogeneously branched linear ethylene interpolymers lack long chain branching, just as is the case for the linear low density polyethylene polymers or linear high density polyethylene polymers. Commercial examples of homogeneously branched linear ethylene/α-olefin interpolymers include TAFMER polymers from the Mitsui Chemical Company, and EXACT and EXCEED polymers from ExxonMobil Chemical Company.

The homogeneously branched substantially linear ethylene/α-olefin interpolymers are described in U.S. Pat. Nos. 5,272,236; 5,278,272; 6,054,544; 6,335,410 and 6,723,810; each incorporated herein by reference. The substantially linear ethylene/α-olefin interpolymers have long chain branching. The long chain branches have the same comonomer distribution as the polymer backbone, and can have about the same length as the length of the polymer backbone. "Substantially linear," typically, is in reference to a polymer that is substituted, on average, with "0.01 long chain branches per 1000 total carbons" to "3 long chain branches per 1000 total carbons." The length of a long chain branch is longer than the carbon length of a short chain branch, formed from the incorporation of one comonomer into the polymer backbone.

Some polymers may be substituted with 0.01 long chain branches per 1000 total carbons to 3 long chain branch per 1000 total carbons, further from 0.01 long chain branches per 1000 total carbons to 2 long chain branch per 1000 total carbons, and further from 0.01 long chain branches per 1000 total carbons to 1 long chain branch per 1000 total carbons.

The substantially linear ethylene/α-olefin interpolymers form a unique class of homogeneously branched ethylene polymers. They differ substantially from the well-known class of conventional, homogeneously branched linear ethylene/α-olefin interpolymers, as discussed above, and, moreover, they are not in the same class as conventional heterogeneous "Ziegler-Natta catalyst polymerized" linear ethylene polymers (for example, ultra low density polyethylene (ULDPE), linear low density polyethylene (LLDPE) or high density polyethylene (HDPE), made, for example, using the technique disclosed by Anderson et al., in U.S. Pat. No. 4,076,698); nor are they in the same class as high pressure, free-radical initiated, highly branched polyethylenes, such as, for example, low density polyethylene (LDPE), ethylene-acrylic acid (EAA) copolymers and ethylene vinyl acetate (EVA) copolymers.

The homogeneously branched, substantially linear ethylene/α-olefin interpolymers useful in the invention have excellent processability, even though they have a relatively narrow molecular weight distribution. Surprisingly, the melt flow ratio (I10/I2), according to ASTM D 1238, of the substantially linear ethylene interpolymers can be varied widely, and essentially independently of the molecular weight distribution (Mw/Mn or MWD). This surprising behavior is contrary to conventional homogeneously branched linear ethylene interpolymers, such as those described, for example, by Elston in U.S. Pat. No. 3,645,992, and heterogeneously branched, conventional "Ziegler-Natta polymerized," linear polyethylene interpolymers, such as those described, for example, by Anderson et al., in U.S. Pat. No. 4,076,698. Unlike substantially linear ethylene interpolymers, linear ethylene interpolymers (whether homogeneously or heterogeneously branched) have rheological properties, such that, as the molecular weight distribution increases, the I10/I2 value also increases.

Long chain branching can be determined by using $^{13}C$ Nuclear Magnetic Resonance (NMR) spectroscopy, and can be quantified using the method of Randall (Rev. Macromol. Chem. Phys., C29 (2 &3), 1989, p. 285-297), the disclosure of which is incorporated herein by reference. Two other methods are Gel Permeation Chromatography, coupled with a Low Angle Laser Light Scattering detector (GPCLALLS), and Gel Permeation Chromatography, coupled with a Differential Viscometer detector (GPC-DV). The use of these techniques for long chain branch detection, and the underlying theories, have been well documented in the literature. See, for example, Zimm, B. H. and Stockmayer, W. H., J. Chem. Phys., 17, 1301 (1949), and Rudin, A., Modern Methods of Polymer Characterization, John Wiley & Sons, New York (1991) pp. 103-112.

In contrast to "substantially linear ethylene polymer," "linear ethylene polymer" means that the polymer lacks measurable or demonstrable long chain branches, that is, the polymer is substituted with an average of less than 0.01 long chain branch per 1000 total carbons.

The ethylene-based polymer may comprise a combination of two or more embodiments as described herein.

The ethylene/α-olefin interpolymer may comprise a combination of two or more embodiments as described herein.

The ethylene/α-olefin copolymer may comprise a combination of two or more embodiments as described herein.

Additives and Applications

An inventive composition may further comprise one or more additives. Typically polymers and resins are treated with one or more stabilizers, for example, antioxidants, such as IRGANOX 1010, IRGANOX 1076, and IRGAFOS 168, each supplied by BASF. Polymers are typically treated with one or more stabilizers before an extrusion or other melt processes. Thus, additives include, but are not limited to, antioxidants, ultraviolet light absorbers, antistatic agents, pigments and dyes, nucleating agents, fillers, fire retardants, tackifiers, plasticizers or oils, smoke inhibitors, viscosity control agents and anti-blocking agents. An inventive composition may also contain one or more thermoplastic polymers.

The inventive compositions may also be used in a variety of applications, including, but not limited to, adhesives, lubricants, dielectric fluids, adhesives, inks, personal care and cosmetic products, sealants, color and additive concentrates.

Definitions

Unless stated to the contrary, all test methods are current as of the filing date of this disclosure.

The term "dative covalent (or coordinate), as used herein, refers to a bond between two atoms, in which the bonding electrons are supplied by one of the two atoms.

The term "composition," as used herein, includes a mixture of materials which comprise the composition, as well as reaction products and decomposition products formed from the materials of the composition.

The term "polymer," as used herein, refers to a polymeric compound prepared by polymerizing monomers, whether of the same or a different type. The generic term polymer thus embraces the term homopolymer (employed to refer to polymers prepared from only one type of monomer, with the understanding that trace amounts of impurities can be incorporated into the polymer structure), and the term interpolymer as defined hereinafter. Trace amounts of impurities, for example, catalyst residues, may be incorporated into and/or within the polymer.

The term "interpolymer," as used herein, refers to polymers prepared by the polymerization of at least two different types of monomers. The generic term interpolymer thus includes copolymers (employed to refer to polymers prepared from two different types of monomers), and polymers prepared from more than two different types of monomers.

The term, "ethylene-based polymer," as used herein, refers to a polymer that comprises, in polymerized form, a majority amount of ethylene monomer (based on the weight of the polymer), and optionally may comprise one or more comonomers.

The term, "ethylene-based interpolymer," as used herein, refers to an interpolymer that comprises, in polymerized form, a majority amount of ethylene monomer (based on the weight of the interpolymer), and at least one comonomer.

The term, "ethylene-based copolymer," as used herein, refers to a copolymer that comprises, in polymerized form, a majority amount of ethylene monomer (based on the weight of the copolymer), and a comonomer, as the only two monomer types.

The term, "ethylene/α-olefin interpolymer," as used herein, refers to an interpolymer that comprises, in polymerized form, a majority amount of ethylene monomer (based on the weight of the interpolymer), and at least one α-olefin.

The term, "ethylene/α-olefin copolymer," as used herein, refers to a copolymer that comprises, in polymerized form, a majority amount of ethylene monomer (based on the weight of the copolymer), and an α-olefin, as the only two monomer types.

The term, "propylene-based polymer," as used herein, refers to a polymer that comprises, in polymerized form, a majority amount of propylene monomer (based on the weight of the polymer), and optionally may comprise one or more comonomers.

The terms "comprising," "including," "having," and their derivatives, are not intended to exclude the presence of any additional component, step or procedure, whether or not the same is specifically disclosed. In order to avoid any doubt, all compositions claimed through use of the term "comprising" may include any additional additive, adjuvant, or compound, whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed.

Test Methods

Melt Viscosity

Melt viscosity is measured in accordance with ASTM D 3236 (177° C., 350° F.), using a Brookfield Digital Viscometer (Model DV-III, version 3), and disposable aluminum sample chambers. The spindle is a SC-31 hot-melt spindle, suitable for measuring viscosities in the range from 10 to 100,000 centipoise (cP). The sample is poured into the chamber, which is, in turn, inserted into a Brookfield Thermosel, and locked into place. The sample chamber has a notch on the bottom that fits the bottom of the Brookfield Thermosel, to ensure that the chamber is not allowed to turn when the spindle is inserted and spinning. The sample (approximately 8-10 grams of resin) is heated to the required temperature, until the melted sample is about one inch below the top of the sample chamber. The viscometer apparatus is lowered, and the spindle submerged into the sample chamber. Lowering is continued, until the brackets on the viscometer align on the Thermosel. The viscometer is turned on, and set to operate at a shear rate, which leads to a torque reading in the range from 40 to 60 percent of the total torque capacity, based on the rpm output of the viscometer. Readings are taken every minute, for about 15 minutes, or until the values stabilize, at which point, a final reading is recorded.

Melt Index

Melt index (I2, or MI) of an ethylene-based polymer is measured in accordance with ASTM D-1238, condition 190° C./2.16 kg. For high I2 polymers (I2 greater than, or equal to, 200 g/mole), the melt index is preferably calculated from Brookfield viscosity as described in U.S. Pat. Nos. 6,335,410; 6,054,544; 6,723,810. I2(190° C./2.16 kg)= $3.6126[10^{(\log(\eta)-60.6928)/-1.1363}]-9.31851$, where η=melt viscosity, in cP, at 350° F.

Gel Permeation Chromatography (GPC)

The average molecular weights and molecular weight distributions for ethylene-based polymers are determined with a chromatographic system, consisting of either a Polymer Laboratories Model PL-210 or a Polymer Laboratories Model PL-220. The column and carousel compartments are operated at 140° C. for ethylene-based polymers. The columns are three Polymer Laboratories 10-micron, Mixed-B columns. The solvent is 1,2,4-trichlorobenzene. The samples are prepared at a concentration of "0.1 gram of polymer" in "50 milliliters" of solvent. The solvent used to prepare the samples contains "200 ppm of butylated hydroxytoluene (BHT)." Samples are prepared by agitating lightly for two hours at 160° C. The injection volume is "100 microliters," and the flow rate is "1.0 milliliters/minute." Calibration of the GPC column set is performed with "narrow molecular weight distribution" polystyrene standards, purchased from Polymer Laboratories (UK). The polystyrene standard peak molecular weights are converted to polyethylene molecular weights, using the following equation (as described in Williams and Ward, J. Polym. Sci., Polym. Let., 6, 621 (1968)):

$$M_{polyethylene}=A\times(M_{polystyrene})^B,$$

where M is the molecular weight, A has a value of 0.4315 and B is equal to 1.0. Polyethylene equivalent molecular weight calculations were performed using VISCOTEK TriSEC software Version 3.0. The molecular weights for propylene-based polymers can be determined using Mark-Houwink ratios according to ASTM D6474.9714-1, where, for polystyrene a=0.702 and log K=−3.9, and for polypropylene, a=0.725 and log K=−3.721. For propylene-based polymer samples, the column and carousel compartments are operated at 160° C.

Differential Scanning Calorimetry (DSC)

Differential Scanning Calorimetry (DSC) is used to measure crystallinity in ethylene (PE)-based polymer samples and propylene (PP)-based polymer samples. About five to eight milligrams of sample is weighed and placed in a DSC pan. The lid is crimped on the pan to ensure a closed atmosphere. The sample pan is placed in a DSC cell, and then heated, at a rate of approximately 10° C./min, to a temperature of 180° C. for PE (230° C. for PP). The sample is kept at this temperature for three minutes. Then the sample is cooled at a rate of 10° C./min to −60° C. for PE (−40° C. for PP), and kept isothermally at that temperature for three minutes. The sample is next heated at a rate of 10° C./min, until complete melting (second heat). The percent crystallinity is calculated by dividing the heat of fusion ($H_f$), determined from the second heat curve, by a theoretical heat of fusion of 292 J/g for PE (165 J/g, for PP), and multiplying this quantity by 100 (e.g., for PE, % cryst.=($H_f$/292 J/g)× 100; and for PP, % cryst.=($H_f$/165 J/g)×100).

Unless otherwise stated, melting point(s) ($T_m$) of each polymer is determined from the second heat curve obtained from DSC, as described above. The crystallization temperature ($T_c$) is measured from the first cooling curve.

Density

Polymer samples that are measured for density are prepared according to ASTM D-1928. Measurements are made within one hour of sample pressing, using ASTM D-792, Method B.

Experimental

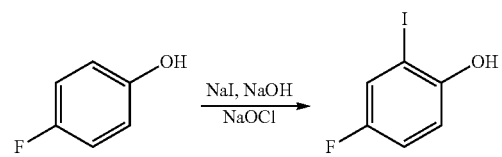

Preparation of 4-fluoro-2-iodophenol

To a round bottom flask, equipped with an addition funnel, and under $N_2$ atmosphere at 0-10° C., was added, methanol (200 mL), 4-fluorophenol (8.00 g, 71.37 mmol), NaI (12.84 g, 85.64 mmol) and NaOH (3.43 g, 85.64 mmol). This solution was allowed to stir for approximately 15 minutes, at 0-10° C., before adding, dropwise, NaOCl (133 mL from 5% v/v in commercial bleach, 92.77 mmol) over the period of 1.5 hours. After this bleach addition was complete, the reaction was allowed to stir for an additional hour at 0-10° C. Next, 100 mL of 10 wt % aqueous sodium thiosulfate was added to the reaction mixture. The reaction mixture was then acidified with 5% HCl, extracted into methylene chloride (500 mL), washed with 500 mL each of 10 wt % aqueous sodium thiosulfate, water, then brine, and then dried over anhydrous magnesium sulfate, filtered through a pad of silica gel, and then concentrated to give an oil. This crude was purified by recrystallization using hexanes, to afford 11.52 g (67.8%) of pure compound as white crystals. $^1$H NMR (500 MHz, Chloroform-d) δ 7.36 (dd, J=7.6, 2.9 Hz, 1H), 6.97 (ddd, J=8.9, 7.7, 2.9 Hz, 2H), 6.92 (dd, J=9.0, 4.9 Hz, 1H), 5.10 (s, 1H). $^{13}$C NMR (101 MHz, Chloroform-d) δ 156.42 (d, J=243.0 Hz), 151.45 (d, J=2.6 Hz), 124.34 (d, J=25.3 Hz), 116.83 (d, J=23.1 Hz), 115.08 (d, J=7.8 Hz), 84.23 (d, J=9.0 Hz). $^{19}$F NMR (376 MHz, Chloroform-d) δ −122.52 (td, J=7.6, 4.9 Hz). MS m/e 238.

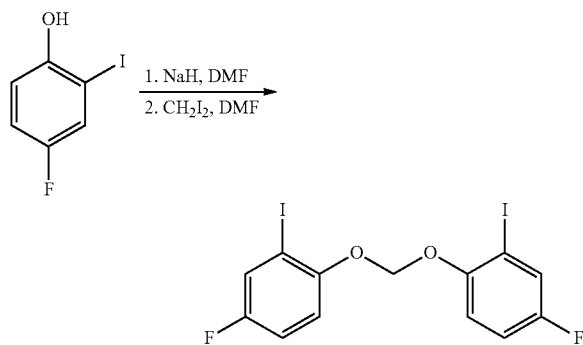

Preparation of bis(4-fluoro-2-iodophenoxy)methane

To a round bottom flask, equipped with an addition funnel, and under N$_2$ atmosphere, was added, N,N-dimethylformamide (120 mL), 4-fluoro-2-iodophenol (5.00 g, 21.01 mmol) and NaH (0.924 g, 23.11 mmol). After stirring for 4 hours, the solution was cooled to 0-10° C. (ice water bath), and a solution of diiodomethane (0.85 mL, 10.10 mmol) in 1 mL of N,N-dimethylformamide was added, dropwise, via addition funnel, over a period of about 5 minutes. The suspension was then carefully heated to 90° C., and maintained that temperature for 18 hours, before cooling to room temperature. Next, diethyl ether (100 mL) was added, and the lowed layer was discarded. The organic ether layer was washed first with 5% aqueous lithium chloride (100 mL), then with 5% aqueous potassium hydroxide (3×50 mL), and finally with brine (50 mL). The organic phase was dried over anhydrous magnesium sulfate, filtered, and concentrated to give colorless crude solid. This crude was recrystallized from hexanes, to afford 4.08 g (79.6%) of product as white crystals. $^1$H NMR (400 MHz, Chloroform-d) δ 7.50 (dd, J=7.6, 3.0 Hz, 2H), 7.18 (dd, J=9.1, 4.7 Hz, 2H), 7.05 (ddd, J=9.1, 7.7, 3.0 Hz, 2H), 5.70 (s, 2H). $^{13}$C NMR (101 MHz, Chloroform-d) δ 159.22, 156.77, 152.28 (d, J=3.0 Hz), 126.20 (d, J=25.0 Hz), 116.10 (m, J=32.0 Hz)), 92.84, 86.82 (d, J=8.2 Hz). $^{19}$F NMR (376 MHz, Chloroform-d) δ −119.43 (td, J=7.8, 4.8 Hz).

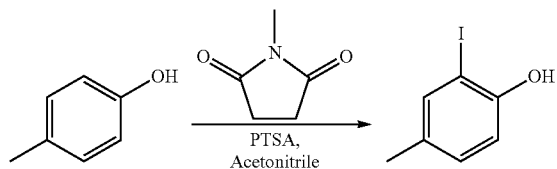

Preparation of 2-iodo-4-methylphenol

To acetonitrile (150 mL), was added, 4-methylphenol (5.00 g, 46.24 mmol) and p-toluenesulfonic acid monohydrate (8.80 g, 46.24 mmol), and this solution was stirred for about 15 minutes at 0-10° C. (ice water bath), at which time, N-iodosuccinimide (10.41 g, 46.27 mmol) was added, and the reaction was stirred for an additional 3 hours at 0-10° C. The reaction flask was placed in a −20° C. freezer for 66 hours, and the PTSA precipitate was filtered off. The filtrate was concentrated to dryness, and dissolved in methylene chloride (200 mL). The organic phase was washed with 200 mL each of 10 wt % aqueous sodium thiosulfate, water, and then brine, and then dried with anhydrous MgSO$_4$, filtered through a pad of silica gel, and then concentrated, to afford 10.81 g (99.9%) of product as a pink oil. $^1$H NMR (400 MHz, Chloroform-d) δ 7.47 (dq, J=2.0, 0.7 Hz, 1H), 7.03 (ddq, J=8.3, 2.1, 0.6 Hz, 1H), 6.87 (d, J=8.3 Hz, 1H), 5.29 (s, 1H), 2.24 (t, J=0.8 Hz, 3H). $^{13}$C NMR (101 MHz, Chloroform-d) δ 152.61, 138.26, 131.92, 130.80, 114.67, 85.37, 19.91. MS m/e 235.

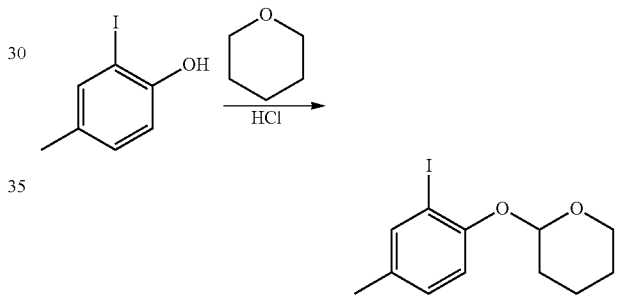

Preparation of 2-(2-iodo-4-methylphenoxy)tetrahydro-2H-pyran

To 2-iodo-4-methylphenol (11.21 g, 47.90 mmol), was added, 3,4-dihydro-2H-pyran (18 mL, 197.29 mmol) and 3 drops of concentrated HCl. The reaction mixture was allowed to stir at room temperature for 3 hours, and then heated at 45° C. for an additional 3 hours, before cooling to room temperature. The reaction mixture was diluted with diethyl ether (100 mL), then washed with 100 mL, each of cold saturated aqueous sodium bicarbonate, water, and then brine, and then dried with anhydrous calcium chloride, filtered through a small pad of silica, and then concentrated to give 15.03 g (98.6%) of product as a golden oil. $^1$H NMR (400 MHz, Chloroform-d) δ 7.59 (d, J=2.0 Hz, 1H), 7.05 (dd, J=8.4, 2.1 Hz, 1H), 6.95 (d, J=8.4 Hz, 1H), 5.46 (t, J=3.0 Hz, 1H), 3.88 (td, J=11.0, 2.9 Hz, 1H), 3.58 (dddd, J=11.3, 4.5, 3.1, 1.6 Hz, 1H), 2.25 (s, 3H), 2.21-2.06 (m, 1H), 2.03-1.92 (m, 1H), 1.92-1.79 (m, 1H), 1.80-1.56 (m, 4H). $^{13}$C NMR (101 MHz, Chloroform-d) δ 153.49, 139.52, 132.95, 129.88, 115.15, 96.73, 87.39, 61.69, 30.23, 25.27, 20.00, 18.34.

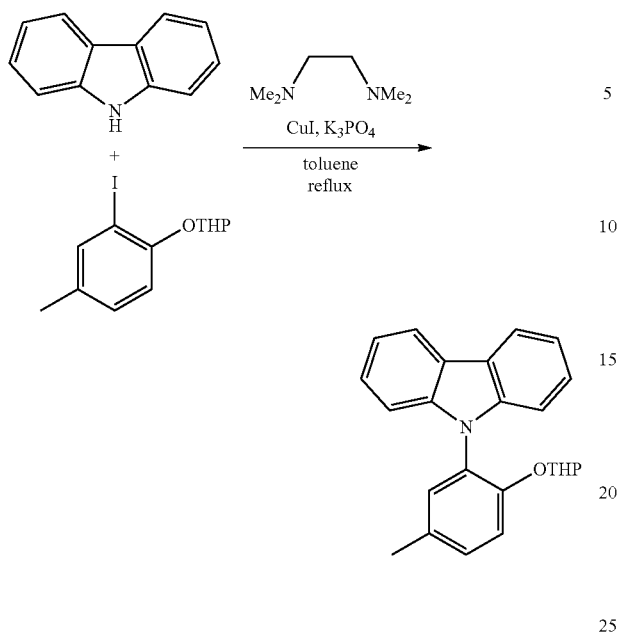

Preparation of 9-(5-methyl-2-((tetrahydro-2H-pyran-2-yl)oxy)phenyl)-9H-carbazole To dry toluene (70 mL), was added, carbazole (4.50 g, 26.91 mmol), 2-(2-iodo-4-methylphenoxy)tetrahydro-2H-pyran (12.00 g, 37.72 mmol), K$_3$PO$_4$ (12.00 g, 56.52 mmol), CuI (0.103 g, 0.541 mmol), and N,N'-dimethylethylenediamine (0.232 mL, 2.15 mmol). The reaction mixture was heated under N$_2$ at 125° C. (heating mantle temperature), for 24 hours, after which time, GC analysis showed 13% conversion. Therefore, additional CuI (0.210 g, 1.10 mmol) and amine (0.464 mL, 4.30 mmol) were added to the reaction, and the reaction was allowed to stir at 125° C., for another 24 hours. After 46 hours total reaction time, GC analysis showed 68% conversion. Therefore, additional CuI (0.210 g, 1.10 mmol) and amine (0.464 mL, 4.30 mmol) were added to the reaction, and the reaction was allowed to stir at 125° C., for another 72 hours. The reaction was cooled, diluted with THF, and filtered by vacuum filtration, through a small pad of silica gel. The filtrate was concentrated, to afford 11.36 g of crude compound, which was purified by flash chromatography, using 2% ethyl acetate in hexanes, to afford 6.10 g (63.4%) of compound, as off white solid. $^1$H NMR (500 MHz, Chloroform-d) δ 8.16 (dt, J=7.6, 1.1 Hz, 2H), 7.40 (dtd, J=8.1, 6.8, 1.2 Hz, 2H), 7.34 (d, J=8.5 Hz, 2H), 7.32-7.24 (m, 4H), 7.22 (dt, J=8.2, 0.9 Hz, 1H), 5.23 (t, J=3.0 Hz, 1H), 3.63 (td, J=11.2, 2.9 Hz, 1H), 3.44 (dddd, J=11.3, 4.5, 3.2, 1.2 Hz, 1H), 2.41 (s, 3H), 1.52-1.35 (m, 2H), 1.30-1.03 (m, 4H). $^{13}$C NMR (101 MHz, Chloroform-d) δ 151.20, 141.42 (d, J=1.4 Hz), 131.94, 129.88 (d, J=17.5 Hz), 126.76, 125.44, 123.13 (d, J=6.5 Hz), 119.93 (d, J=5.9 Hz), 119.34 (d, J=0.9 Hz), 117.43, 110.40 (d, J=35.3 Hz), 97.08, 61.48, 29.91, 24.93, 20.53, 17.61. MS m/e 380 (M+Na).

Preparation of 9-(5-methyl-2-((tetrahydro-2H-pyran-2-yl)oxy)-3-(4,4,5,5-tetramethyl-1,3,2-dioxaborolan-2-yl)phenyl)-9H-carbazole To an oven dried, three-necked, round-bottomed flask at 0-10° C., and under N$_2$ atmosphere, was added, 9-(5-methyl-2-((tetrahydro-2H-pyran-2-yl)oxy)phenyl)-9H-carbazole (11.90 g, 33.29 mmol) and dry tetrahydrofuran (250 mL). This solution was cooled to 0-10° C. (ice-water bath) for about 15 minutes, and 2.5 M n-butyllithium, in hexanes (20 mL, 50.00 mmol), was added slowly. After stirring for 4 hours, 2-iso-propoxy-4,4,5,5-tetramethyl-1,3,2-dioxaborolane (10.2 mL, 49.94 mmol) was added slowly. The mixture was stirred for one hour at 0-10° C., before allowing the reaction to warm to room temperature, and then stirred for an additional 18 hours. To the reaction mixture, was added, cold saturated aqueous sodium bicarbonate (100 mL). The mixture was extracted with four 50 mL portions of methylene chloride. The organic phases were combined, and washed with cold saturated aqueous sodium bicarbonate (200 mL), brine (200 mL), and then dried over anhydrous magnesium sulfate, filtered, and concentrated to give crude as a golden foam. This crude was slurried in acetonitrile (50 mL), and allowed to sit for an hour at room temperature, before isolating the solid by vacuum filtration. The solids were washed with a small portion of cold acetonitrile, and dried under high vacuum, to afford 13.44 g (83.5%) of the product as a white powder. $^1$H NMR (400 MHz, Chloroform-d) δ 8.14-8.08 (m, 2H), 7.71 (dd, J=2.4, 0.8 Hz, 1H), 7.44-7.35 (m, 2H), 7.33-7.22 (m, 5H), 4.90 (t, J=2.9 Hz, 1H), 2.63 (ddd, J=11.3, 10.1, 3.0 Hz, 1H), 2.59-2.51 (m, 1H), 2.38 (s, 3H), 1.77-1.64 (m, 1H), 1.40 (d, J=4.6 Hz, 12H), 1.35-1.07 (m, 4H), 1.02-0.89 (m, 1H). $^{13}$C NMR (101 MHz, Chloroform-d) δ 156.51, 141.22 (d, J=7.2 Hz), 137.32, 133.69, 132.91, 130.02, 125.62, 123.25, 122.93, 119.75 (d, J=1.2 Hz), 119.38 (d, J=3.1 Hz), 110.92, 110.69, 101.79, 83.79, 61.22, 29.96, 24.91, 24.87 (d, J=28.9 Hz), 20.42, 18.22. MS m/e 507 (M+Na).

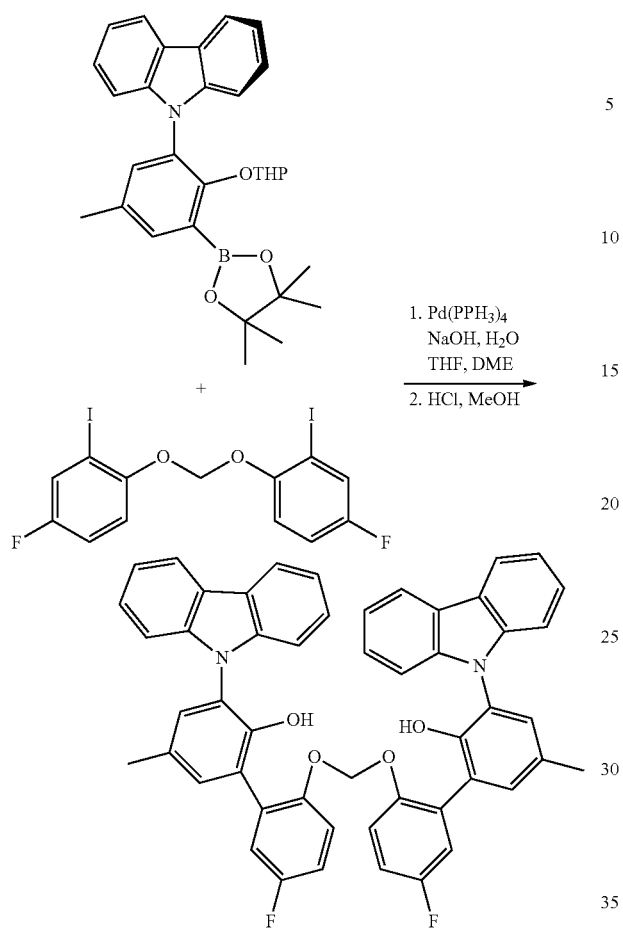

Preparation of 6',6'''-(methylenebis(oxy))bis(3-(9H-carbazol-9-yl)-3'-fluoro-5-methyl-[1,1'-biphenyl]-2-ol)

To a round bottom flask, under $N_2$ atmosphere, was added, 9-(5-methyl-2-((tetrahydro-2H-pyran-2-yl)oxy)-3-(4,4,5,5-tetramethyl-1,3,2-dioxaborolan-2-yl)phenyl)-9H-carbazole (8.58 g, 17.25 mmol) (mmol adjusted based on a purity of 97.2% by HPLC), dimethoxyethane (200 mL), a solution of NaOH (2.16 g, 54.00 mmol) in water (60 mL), tetrahydrofuran (60 mL), and bis(4-fluoro-2-iodophenoxy)methane (4.00 g, 8.20 mmol). The system was purged with $N_2$ for approximately 15 minutes, and Pd(PPh$_3$)$_4$ (468 mg, 0.41 mmol) was added. The mixture was heated to reflux at 85° C., for 24 hours, and then allowed to cool to room temperature. Once cooled, a precipitate was formed in the reaction flask, which was isolated by vacuum filtration, and dried under high vacuum, for one hour, to afford crude protected ligand. The crude protected ligand was slurried in a mixture of tetrahydrofuran (500 mL) and methanol (250 mL), and then heated to 60° C. To the slurry, was added, concentrated HCl, until the solution became acidic according to pH paper, and then stirred at 60° C. for 8 hours (as the deprotection progressed all of the precipitate gradually went into solution), and then allowed to cool and then concentrated. The residue was dissolved in methylene chloride (500 mL), washed with brine (500 mL), dried over anhydrous magnesium sulfate, filtered through a pad of silica gel, and then concentrated to afford 5.65 g (88.5%) of ligand. $^1$H NMR (400 MHz, DMSO-d6) δ 7.80 (s, 2H), 7.39 (ddd, J=7.7, 1.2, 0.7 Hz, 4H), 6.60-6.52 (m, 4H), 6.50-6.36 (m, 12H), 6.29 (ddd, J=23.0, 2.3, 0.7 Hz, 4H), 6.16 (ddd, J=9.1, 8.2, 3.2 Hz, 12H), 4.92 (s, 2H), 1.45 (s, 6H). $^{13}$C NMR (101 MHz, DMSO-d6) δ 157.33 (d, J=238.4 Hz), 151.00 (d, J=2.2 Hz), 148.88, 140.97, 131.82, 130.32 (d, J=8.2 Hz), 128.77 (d, J=18.1 Hz), 127.05 (d, J=1.3 Hz), 125.99, 124.40, 123.15, 120.35, 119.61, 118.04, 117.81, 117.27 (d, J=8.5 Hz), 115.13, 114.90, 110.43, 20.07. $^{19}$F NMR (376 MHz, DMSO-d6) δ −121.60 (td, J=8.6, 4.8 Hz). MS m/e 796 (M+NH$_4$).

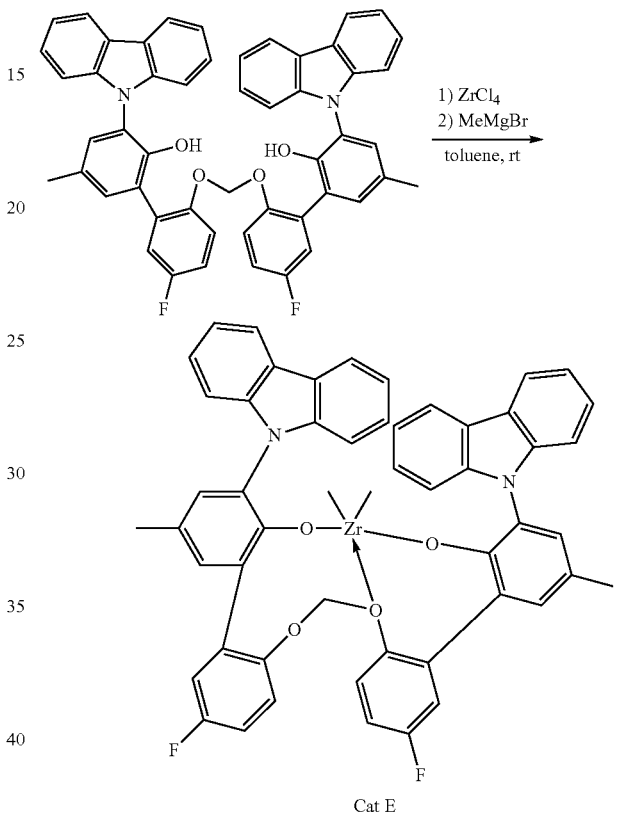

Preparation of Cat E

The ligand (0.500 g, 0.64 mmol) was mixed with 40 mL toluene in a drybox. The ZrCl$_4$ (0.150 g, 0.64 mmol) was suspended in 10 mL toluene, and quickly added to the stirred solution of the ligand. The MeMgBr (0.96 mL, 2.89 mmol; 3M solution in diethyl ether) was added dropwise via a syringe. The color of the reaction mixture turned black during the addition of the Grignard reagent. The mixture was stirred for 2 hours. The suspension was filtered through a 0.45 micron PTFE syringe filter, and then the filtrate was reduced to dryness under vacuum. The residue was mixed with 10 mL toluene and 5 mL hexane, filtered (0.45 micron), and the filtrate was concentrated to about 5 mL, under vacuum, filtered, and the filtrate was mixed with excess hexane (~15 mL) to form an off-white precipitate, which was filtered and dried under vacuum. The product was dissolved in 10 mL toluene, and 4-5 mL hexane was added, causing a light brown precipitate, which was filtered off and discarded. The filtrate was layered with hexane, and cooled to −20° C., causing a white precipitate, which was filtered and dried under vacuum (215 mg, 37%). For catalyst E, one oxygen (Z1 or Z2 location) is dative covalent bonded to the Zr. $^1$H NMR (400 MHz, $C_6D_6$) δ 8.02 (d, J=7.7 Hz, 2H), 7.94 (d, J=7.8 Hz, 2H), 7.27 (m, 8H), 7.15 (m, 2H), 6.99 (m, 4H), 6.88 (d, J=2.2 Hz, 2H), 6.83 (m, 2H), 6.16 (m, 4H), 4.72 (s, 2H), 2.14 (s, 6H), −1.12 (s, 6H). $^{13}$C{$^1$H} NMR (101 MHz, $C_6D_6$) δ 162.03, 159.58, 154.88, 147.33, 147.30, 142.32, 142.14, 134.42, 134.34, 131.00, 130.94, 130.34, 129.59, 129.58, 127.35, 126.91, 126.70, 124.93, 123.95, 122.06, 121.25, 120.73, 120.59, 120.50, 119.96, 119.72, 116.28, 116.05, 111.92, 109.61, 96.74, 44.04, 21.09.

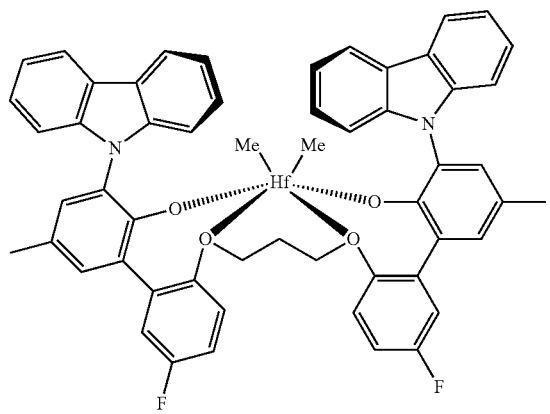

Cat B

Ligand synthesis utilized the reaction steps outlined for the synthesis of the ligand for Cat E except for the difference in the synthetic step that generated the bottom bridge fragment. In order to accomplish this, the preparation of bis(4-fluoro-2-iodophenoxy)methane was replaced by the following synthetic step:

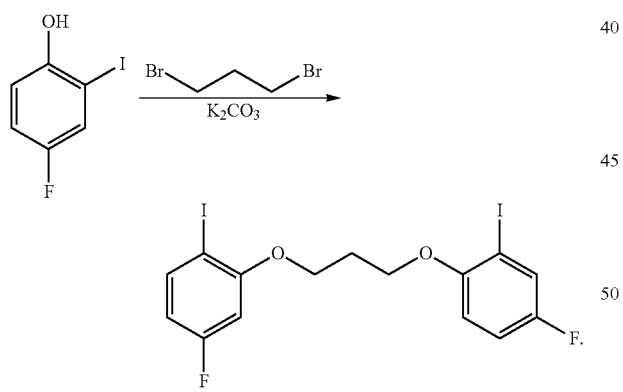

Preparation of 1,3-bis(4-fluoro-2-iodophenoxy)propane

A 500 mL flask was charged with 4-fluoro-2-iodophenol (15.00 g, 63.03 mmol), 1,3-dibromopropane (6.40 g, 31.68 mmol), $K_2CO_3$ (26.00 g, 188.4 mmol) and acetone (200 mL). The reaction mixture was stirred and refluxed for 24 hours. The mixture was cooled and filtered. The filtrate was concentrated by rotary evaporation. The resulting solid was recrystallized from acetonitrile, to afford the desired product as white crystals (12.00 g, 74%). $^1$H NMR (300 MHz, Chloroform-d) δ 7.48 (m, 1H), 7.02 (m, 1H), 6.88 (m, 1H), 4.26 (t, J=6.05 Hz, 4H) and 2.34 (quintet, J=6.05 Hz, 2H). Ms m/e 516.

Cat B was synthesized using the procedure described for Cat E, with the exception that $ZrCl_4$ was replaced by $HfCl_4$ as shown below.

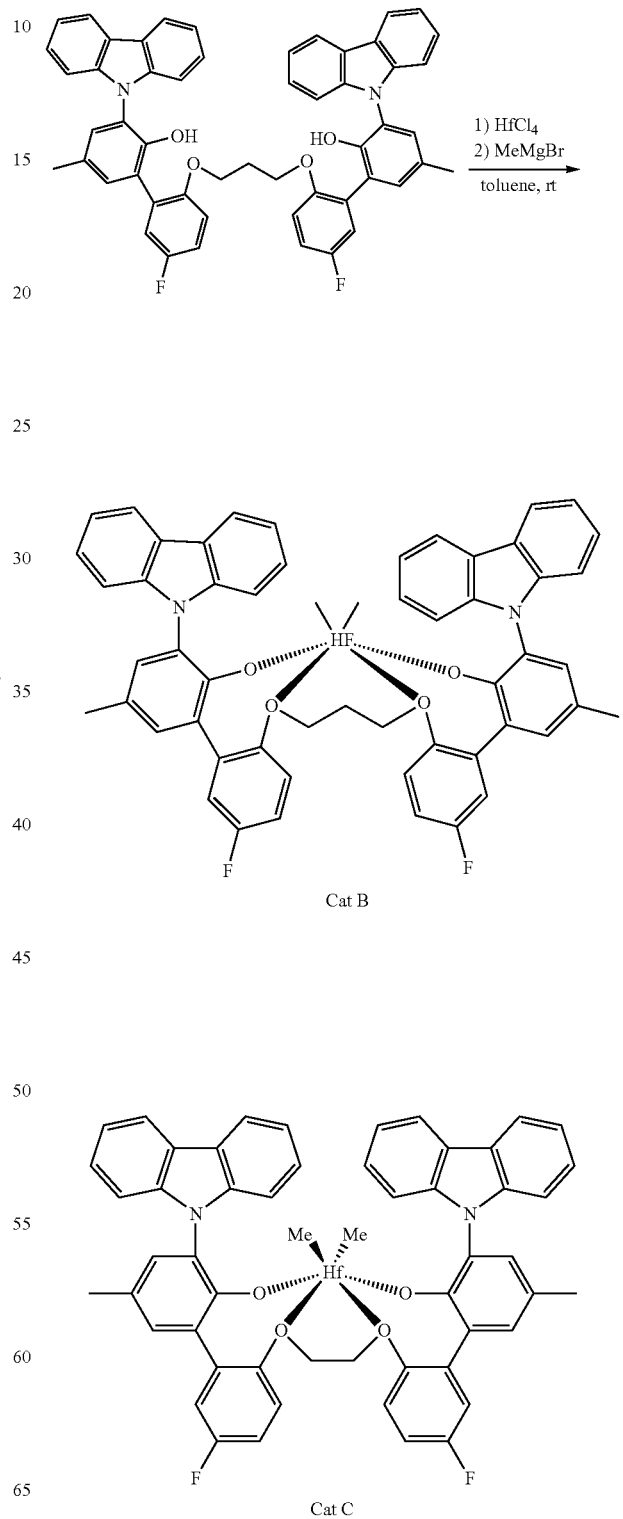

-continued

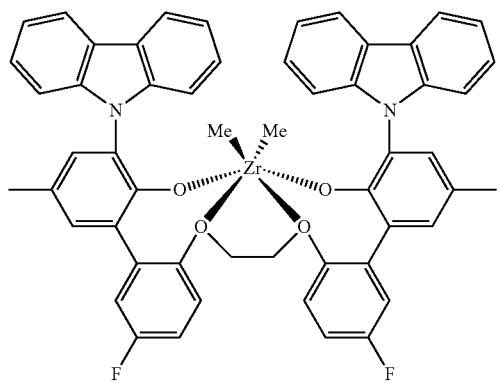

Cat D

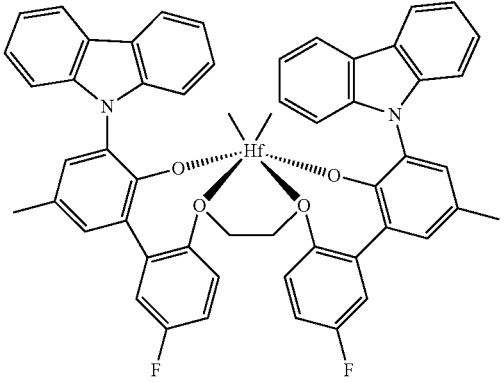

Cat C

Ligand synthesis utilized the reaction steps outlined for the synthesis of the ligand for Cat E, except for the difference in the synthetic step that generated the bottom bridge fragment. In order to accomplish this, the preparation of bis(4-fluoro-2-iodophenoxy)methane was replaced by the preparation of 1,2-bis(4-fluoro-2-iodophenoxy)ethane, as shown below. This step was carried out following the procedure described for the synthesis of 1,3-bis(4-fluoro-2-iodophenoxy)propane:

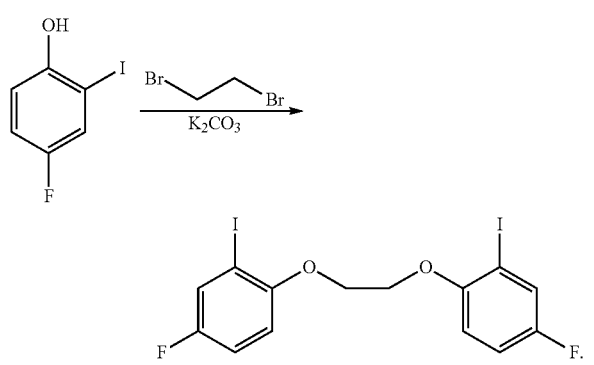

Cat C was synthesized using the procedure described for Cat B as shown below:

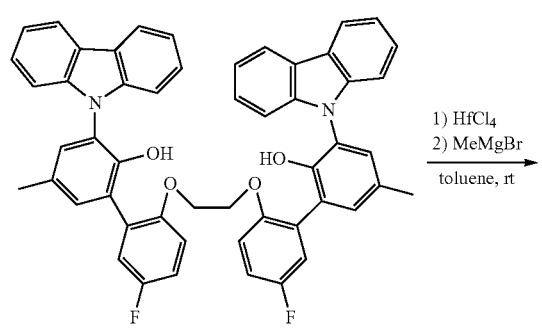

Cat D was synthesized using the procedure described for Cat E as shown below:

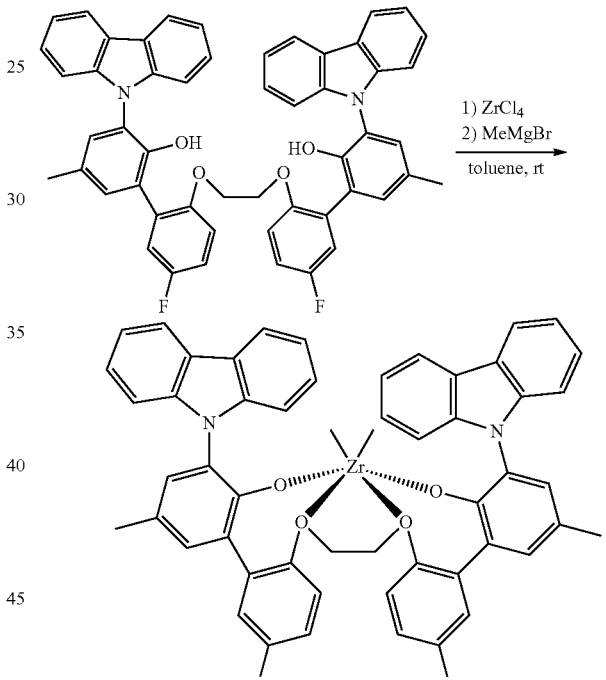

Cat D

Experimental for Ethylene/1-Octene Polymerizations

The ethylene/octene copolymerizations were conducted in a 2 L Parr batch reactor. The reactor was heated by an electrical heating mantle, and cooled by an internal serpentine cooling coil containing cooling water. Both the reactor and the heating/cooling system were controlled and monitored by a CAMILE TG process computer. The bottom of the reactor was fitted with a dump valve, which emptied the reactor contents into a SS dump pot, which was prefilled with a catalyst kill solution. The dump pot was vented to a 30 gallon blowndown tank, with both the pot and the tank $N_2$ purged. All chemicals (ethylene, 1-octene, toluene and mixed alkanes solvent ISOPAR E (from ExxonMobil)) used for polymerization or catalyst makeup were run through purification columns, to remove any impurities that could affect polymerization. The $N_2$, used for transfers, was also passed through a column to remove impurities.

The reactor was loaded first from the shot tank containing ISOPAR E and 1-octene. The shot tank was filled to the load set points by use of a lab scale, on which the tank was mounted. After solvent addition, the reactor was heated up to the polymerization temperature set point. Ethylene was added to the reactor when at reaction temperature, to maintain reaction pressure set point. Ethylene addition amounts were monitored by a micro-motion flow meter.

The catalyst and the cocat-2 activator (1.2 equiv.) were mixed with the appropriate amount of toluene to achieve a desired molarity solution. The catalyst and activator were handled in an inert atmosphere glovebox, drawn into a syringe, and then pressure transferred into the catalyst shot tank. This was followed by 3 rinses of toluene (5 mL each). Before the ethylene addition, 10 moles of cocat-1 (MMAO) was added to the reactor through the catalyst shot tank. Catalyst and activator were added when the reactor pressure setpoint was achieved.

Immediately after catalyst addition the run timer started. Usually within the first 2 minutes of successful catalyst runs, an exotherm was observed, as well as decreasing reactor pressure. Ethylene was then added by the CAMILE (process control software, version 5), to maintain the reaction pressure setpoint in the reactor. These polymerizations were run for 10 minutes, then the agitator was stopped, and the bottom dump valve opened to empty the reactor contents to the dump pot. The dump pot contents were poured into trays, which were placed in a lab hood, where the solvent was evaporated off overnight. The trays containing the residual polymer were then transferred to a vacuum oven, where they were heated up to 140° C., under vacuum, to remove any remaining solvent. After the trays cool to ambient temperature, the polymers were weighed for yield/efficiencies. Polymerization results are shown in Table 1.

ues (>50° C.). Thus, the inventive complexes can be used to produce very low molecular weight polymers, such as wax components, useful for hot melt adhesives, and other types of adhesives.

The invention claimed is:

1. A molecular transition metal complex represented by Formula 1:

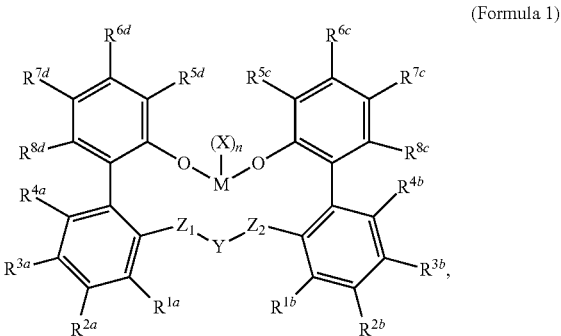

(Formula 1)

wherein M is zirconium or hafnium, each independently being in a formal oxidation state of +4;

n is 2;

each X is independently a monoanionic ligand $Z_1$ and $Z_2$ are each independently selected from —O— or —S—;

Y is a single atom bridge selected from the following: —$CR_2$—, —$GeR_2$—, —$SiR_2$—, —PR—, —NR—; wherein each R is independently a hydrogen, a substituted or unsubstituted ($C_1$-$C_{40}$)hydrocarbyl, a substituted or unsubstituted ($C_1$-$C_{40}$)heterohydrocarbyl, or —$OR^C$;

TABLE 1

Polymerization Results

| Catalyst | | | Exotherm | Efficiency (g polymer per | Tm | Mw | | Octene |
|---|---|---|---|---|---|---|---|---|
| Name | μmol | Metal | (° C.) | g metal) | (° C.) | (g/mole) | Mw/Mn | mol % |
| CAT B[b] Comparative | 0.04 | Hf | 1.8 | 7,815,564 | −27.3 | 466,063 | 2.28 | 33.4 |
| CAT C[b] Comparative | 0.15 | Hf | 4.1 | 3,040,320 | −36.6 | 2,399 | 1.99 | 31.7 |
| CAT D[b] Comparative | 0.08 | Zr | 1.9 | 4,014,843 | NA | 733* | 1.57 | 36.7 |
| CAT E[b] Inventive | 0.10 | Zr | 2.0 | 1,161,975 | 74.5 | 671 | 1.73 | 11.5 |

[b]Polymerization conditions: 2 L batch reactor, temperature: 140° C.; ISOPAR-E: 605 g; 1-octene: 300 g; ethylene pressure: 288 psi; run time: 10 min; Cocat-2: 1.2 equiv; Cocat-1 = MMAO-3A: 10 μmoles.
*A liquid.
NA: Tm could not be detected.

Cocat-1: MMAO

Cocat-2: methylbis(octadecyl)ammonium tetrakis(pentafluorophenyl)borate, [HNMe($C_{18}H_{37}$)$_2$][B($C_6F_5$)$_4$].

The results detailed herein demonstrate that the inventive transition metal complexes, represented by Formula 1, are highly active for the production of very low molecular weight ethylene-based polymers at 140° C., with good efficiencies to allow for increased reactor throughput. Furthermore, these ethylene-based polymers has high Tm val- $R^{1a}$, $R^{2a}$, $R^{3a}$, $R^{4a}$, $R^{1b}$, $R^{2b}$, $R^{3b}$, $R^{4b}$, $R^{6c}$, $R^{7c}$, $R^{8c}$, $R^{6d}$, $R^{7d}$, and $R^{8d}$ are each, independently, selected from: a substituted or unsubstituted ($C_1$-$C_{10}$)alkyl, a halogen, or a hydrogen; and wherein each $R^C$ is independently a substituted or unsubstituted ($C_1$-$C_{30}$)hydrocarbyl, or a substituted or unsubstituted ($C_1$-$C_{30}$) heterohydrocarbyl; and $R^{5c}$ and $R^{5d}$ are each, independently, selected from the following groups g1) through g14):

g1)
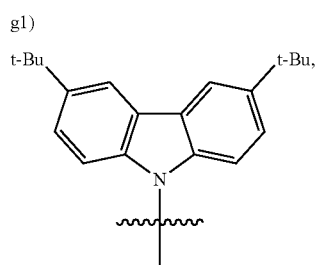
g2)
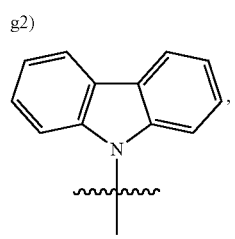
g3)
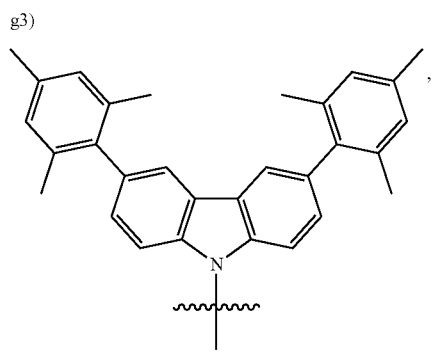
g4)
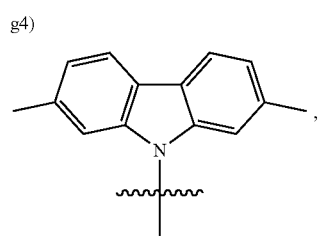
g5)
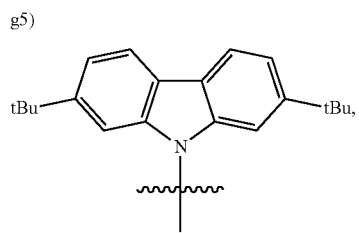
g6)
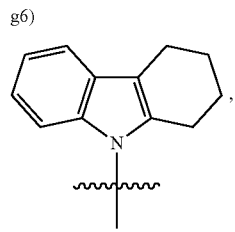
-continued
g7)
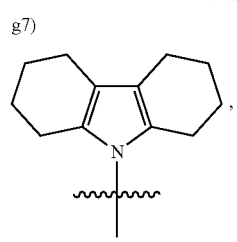
g8)
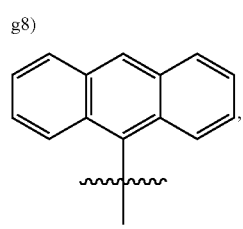
g9)
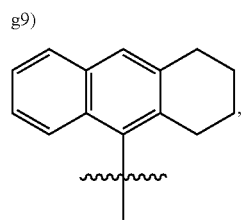
g10)
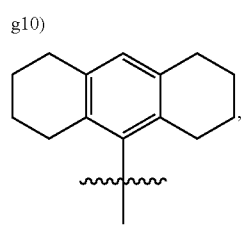
g11)
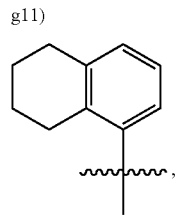
g12)
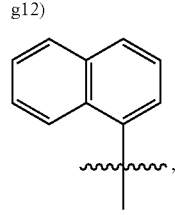
g13)
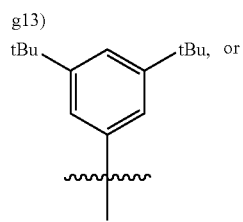

g14)

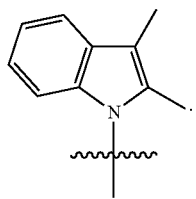

and wherein either $Z_1$ or $Z_2$ is dative covalent (coordinate) to M.

2. The molecular transition metal complex of claim 1, wherein each Z is —O— (oxygen atom).

3. The molecular transition metal complex of claim 1, wherein each X is independently an alkyl.

4. The molecular transition metal complex of claim 3, wherein each X is independently a $(C_1$-$C_7)$alkyl.

5. The molecular transition metal complex of claim 1, wherein Y is selected from the following: —CHR—, —CRR'—, —CR$_2$—, —CH$_2$—; and wherein each R is independently an alkyl or an aryl, and wherein each R' is independently an alkyl or an aryl.

6. The molecular transition metal complex of claim 1, wherein $R^{3a}$ or $R^{3b}$ are each, independently, selected from a halogen, an amine, alkoxy, or an alkyl.

7. The molecular transition metal complex of claim 1, wherein $R^{1a}$, $R^{2a}$, $R^{4a}$, $R^{1b}$, $R^{2b}$, $R^{4b}$, $R^{6c}$, $R^{8c}$, $R^{6d}$ and $R^{8d}$ are each hydrogen.

8. A process to form an ethylene-based polymer, said process comprising polymerizing a mixture comprising ethylene, and optionally at least one comonomer, in the presence of at least one molecular transition metal complex of claim 1, which is rendered catalytically active by contacting it to, or combining it with, an activating cocatalyst.

9. A catalyst system comprising one or more than one procatalyst having a structure according to any of a) through ee):

a)

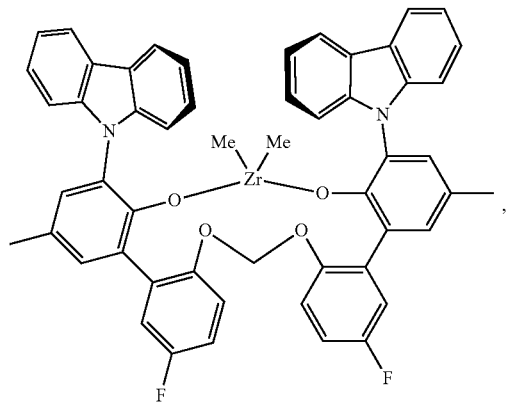

b)

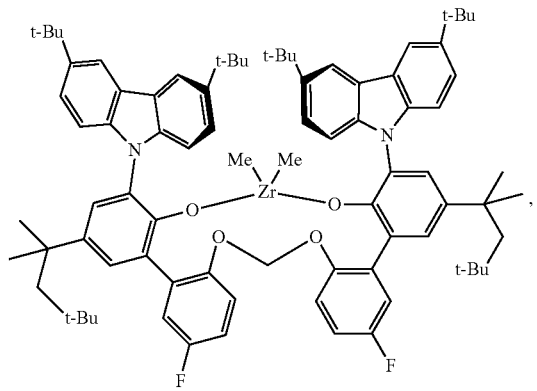

c)

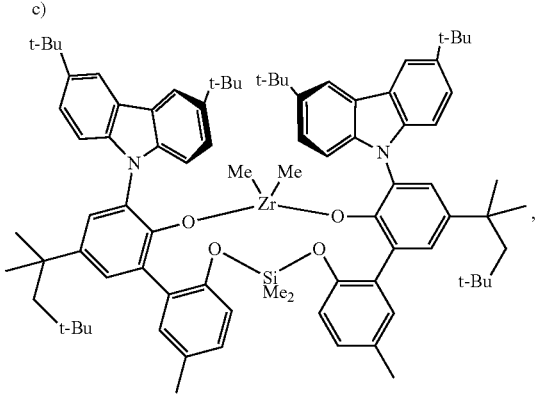

d)

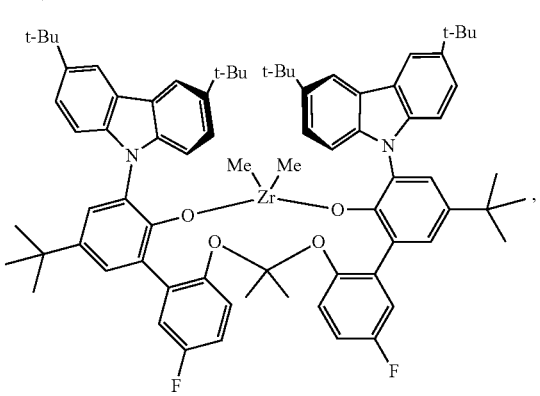

e)

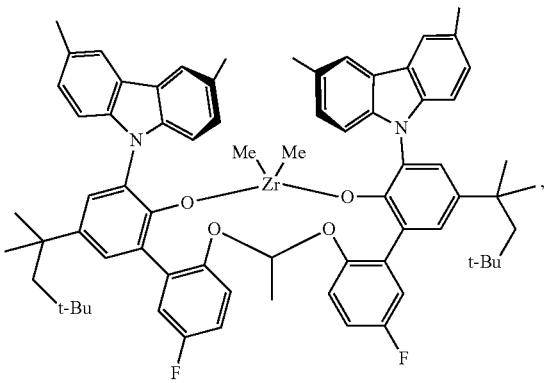

-continued
f)
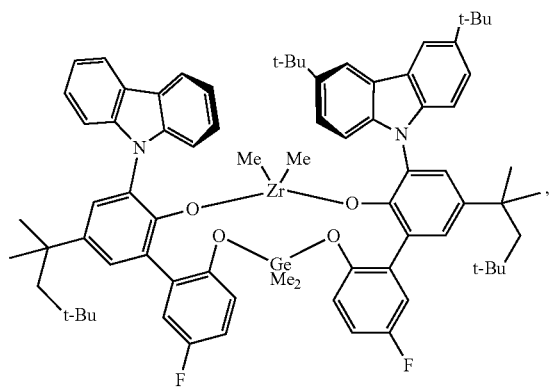
g)
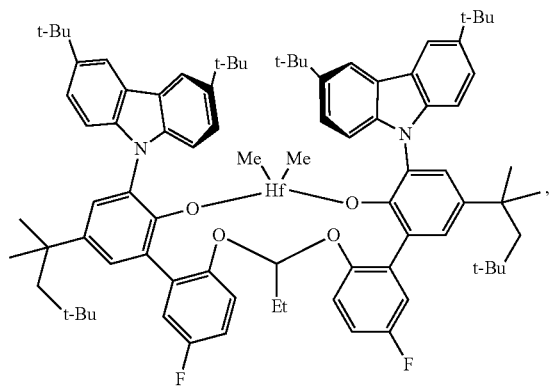
h)
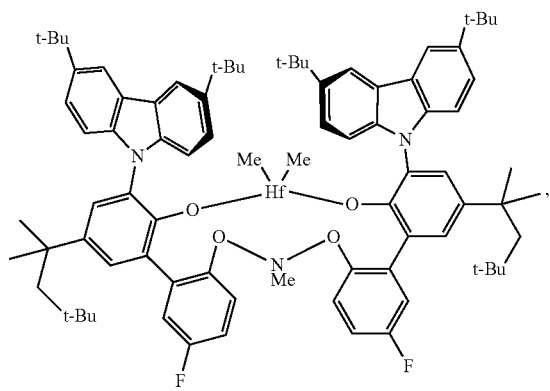
i)
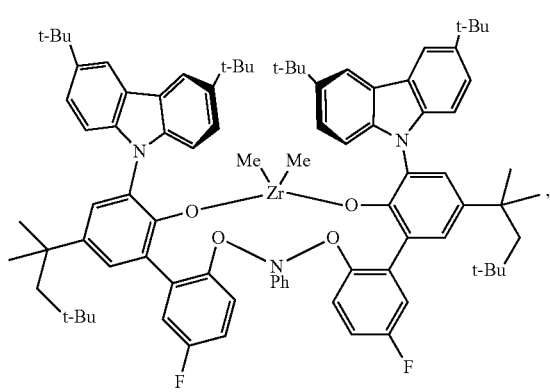
j)
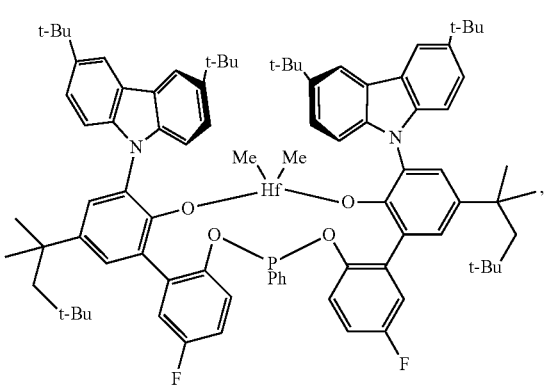
k)
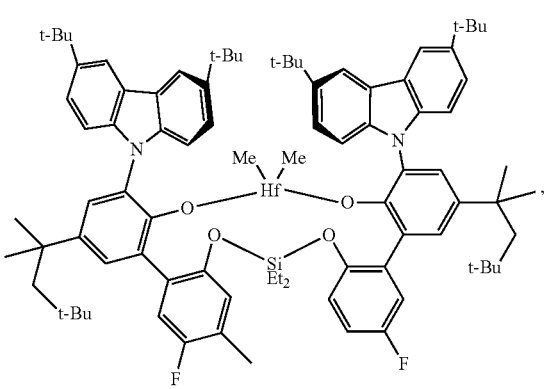
l)
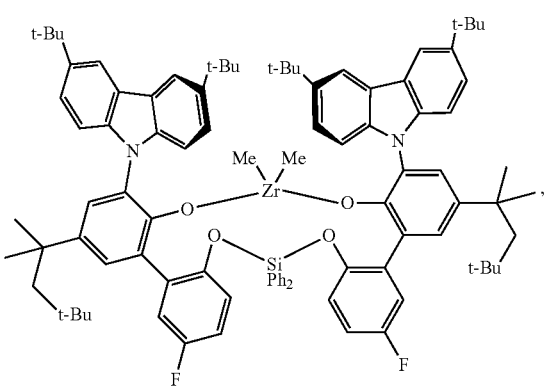
m)
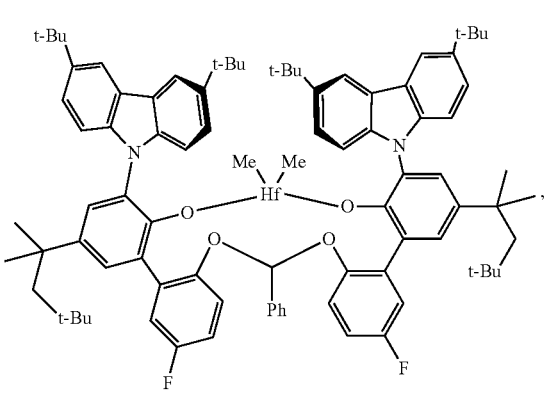

n)
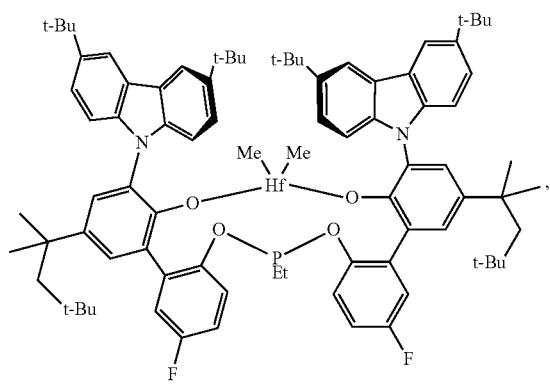
o)
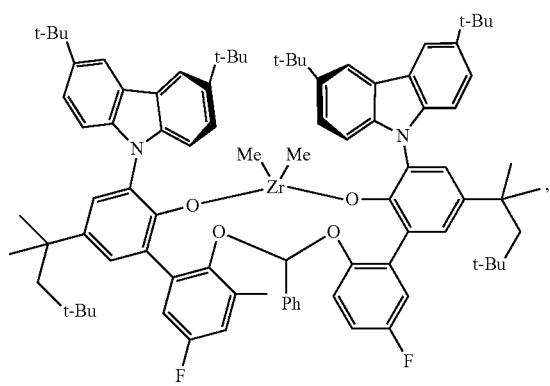
p)
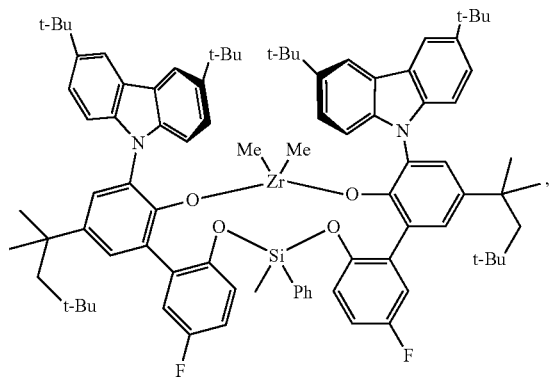
q)
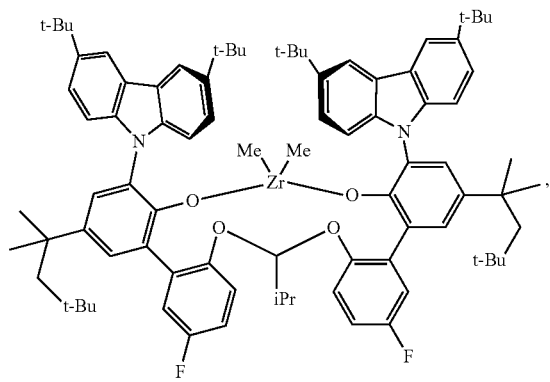
r)
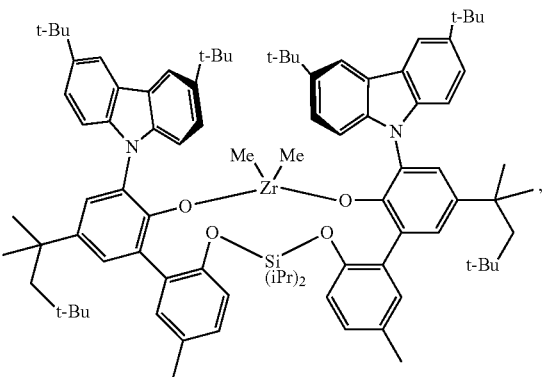
s)
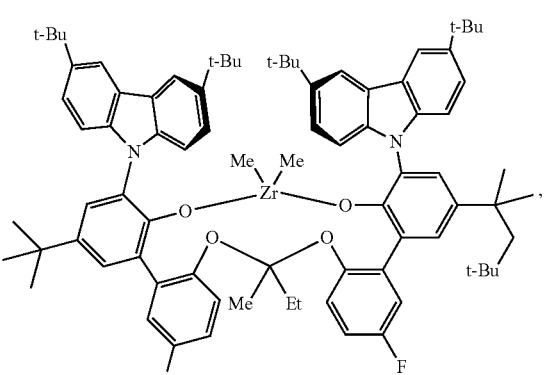
t)
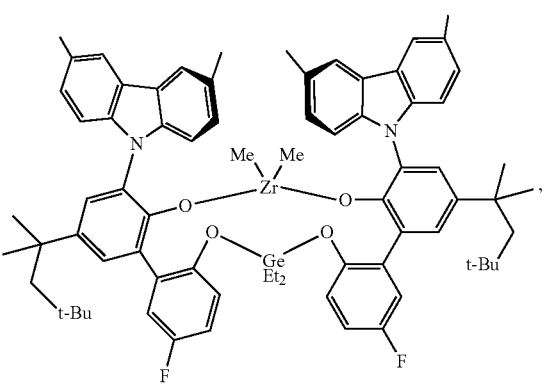
u)
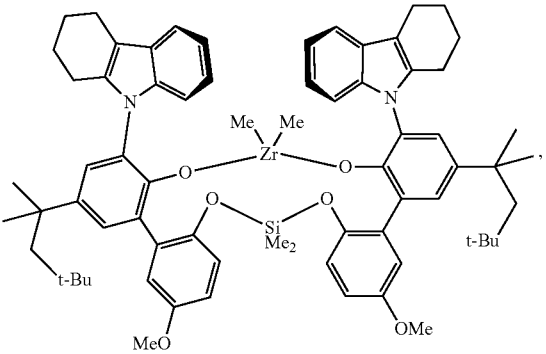

-continued
v)
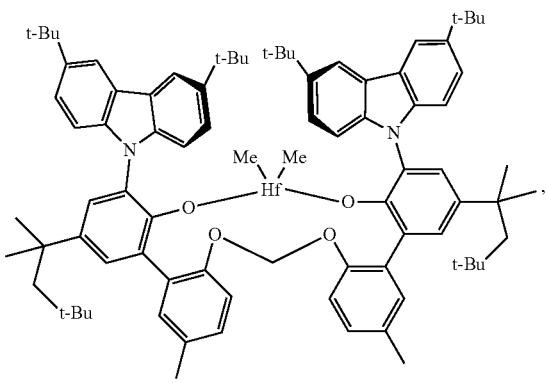
w)
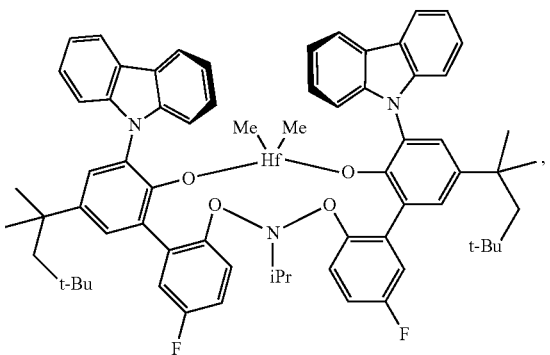
x)
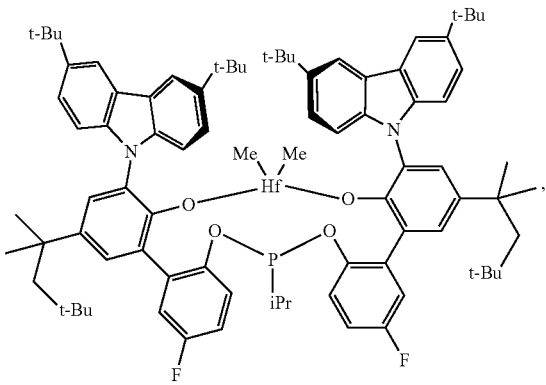
y)
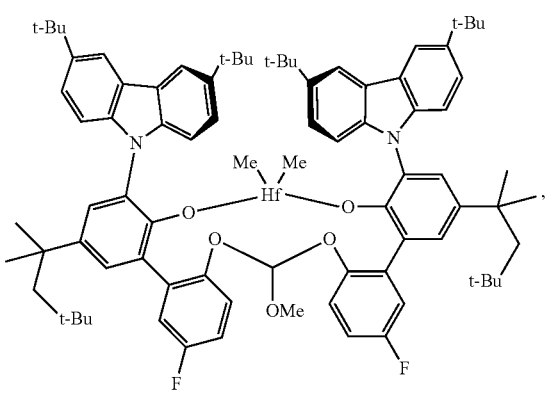
-continued
z)
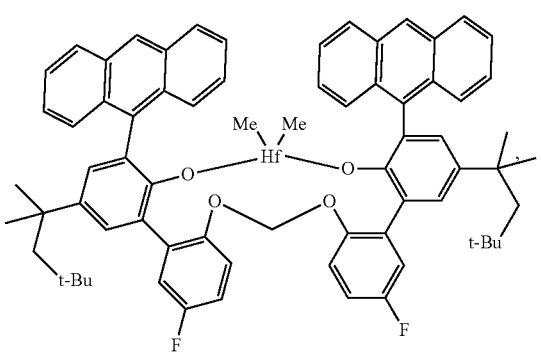
aa)
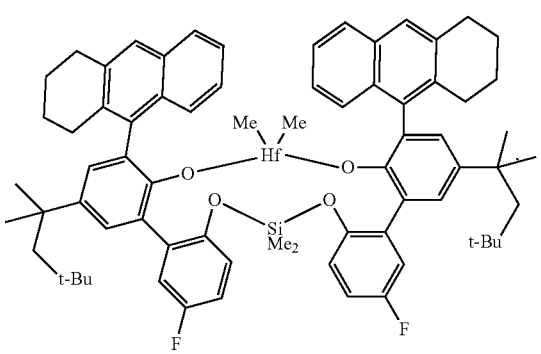
bb)
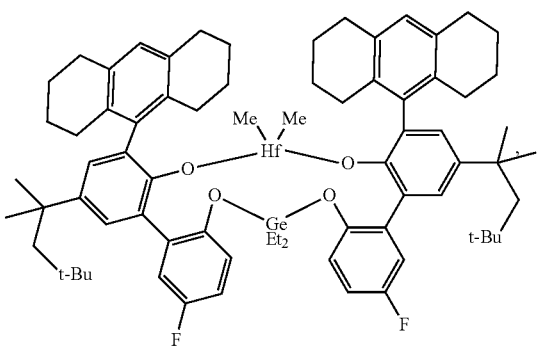
cc)
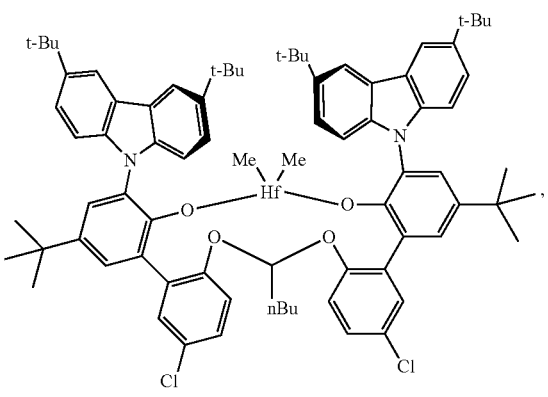

dd)
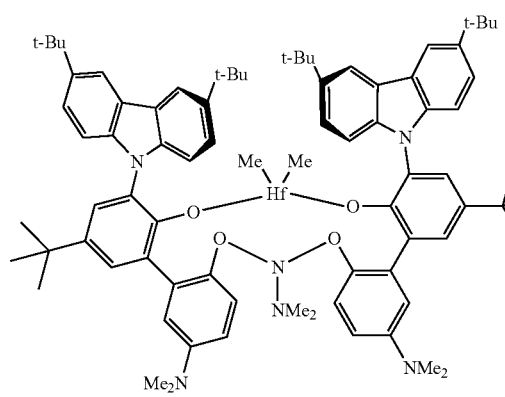
, or
ee)
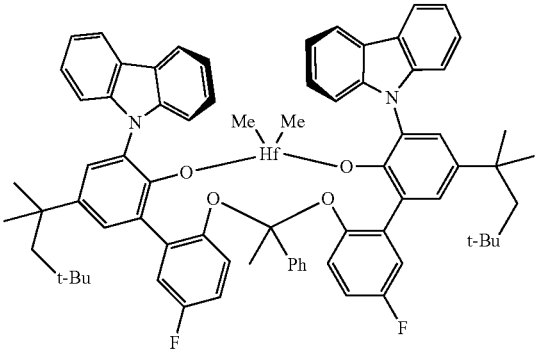
.
* * * * *